(12) United States Patent
Thomsen et al.

(10) Patent No.: US 10,667,798 B2
(45) Date of Patent: Jun. 2, 2020

(54) SURGICAL TOOL HANDLE ASSEMBLIES AND RELATED METHODS

(71) Applicant: Zimmer, Inc., Warsaw, IN (US)

(72) Inventors: Darren Thomsen, Warsaw, IN (US); Walter W. Thomas, Warsaw, IN (US); Andrew J. Steiner, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 1370 days.

(21) Appl. No.: 14/062,286

(22) Filed: Oct. 24, 2013

(65) Prior Publication Data

US 2014/0121650 A1    May 1, 2014

Related U.S. Application Data

(60) Provisional application No. 61/719,709, filed on Oct. 29, 2012, provisional application No. 61/800,423, filed on Mar. 15, 2013.

(51) Int. Cl.
*A61B 17/00* (2006.01)
*A61B 17/16* (2006.01)

(52) U.S. Cl.
CPC .......... *A61B 17/00* (2013.01); *A61B 17/1659* (2013.01); *A61B 2017/0046* (2013.01)

(58) Field of Classification Search
CPC ........ A61B 17/1659; A61B 2017/0046; A61B 17/58; A61B 17/60; B60J 7/185; Y10T 403/589; Y10T 403/59; Y10T 403/591; Y10T 403/593; Y10T 403/599; Y10T 403/33

USPC ......... 606/1, 80, 85, 99; 292/217; 74/53, 54, 74/55; 403/321
See application file for complete search history.

(56) References Cited

U.S. PATENT DOCUMENTS

| | | |
|---|---|---|
| 4,583,270 A | 4/1986 | Kenna |
| 4,587,964 A | 5/1986 | Walker et al. |
| 4,601,289 A | 7/1986 | Chiarizzio et al. |
| 4,765,328 A | 8/1988 | Keller et al. |
| 4,922,574 A | 5/1990 | Heiligenthal et al. |
| 4,990,149 A | 2/1991 | Fallin |
| 5,089,033 A | 2/1992 | Wijmans |
| 5,190,549 A | 3/1993 | Miller et al. |
| 5,190,550 A | 3/1993 | Miller et al. |

(Continued)

FOREIGN PATENT DOCUMENTS

| | | |
|---|---|---|
| EP | 0496629 A1 | 7/1992 |
| EP | 1854416 A1 | 10/1994 |
| EP | 1011902 B1 | 12/2001 |

*Primary Examiner* — Michael W Kahelin
*Assistant Examiner* — Vynn V Huh
(74) *Attorney, Agent, or Firm* — Schwegman Lundberg & Woessner, P.A.

(57) ABSTRACT

A surgical tool handle assembly can include a handle body and a tool locking mechanism. The handle body can have a tool receiving end for receiving a mating end of a surgical tool. The tool locking mechanism can be configured to securely engage the surgical tool mating end, thereby locking the surgical tool to the handle. The locking mechanism can include a ramp feature, a locking cam, and an actuation mechanism. The actuation mechanism can be configured to actuate the cam to engage the ramp feature as the cam engages the tool mating end to lock the tool to the handle. A surgical kit and a method of locking a surgical tool to a tool handle are also disclosed.

17 Claims, 40 Drawing Sheets

(56) References Cited

U.S. PATENT DOCUMENTS

| | | | |
|---|---|---|---|
| 5,261,915 A | 11/1993 | Durlacher et al. | |
| 5,324,293 A | 6/1994 | Rehmann | |
| 5,350,381 A | 9/1994 | Melton | |
| 5,531,750 A * | 7/1996 | Even-Esh | A61B 17/1659 606/79 |
| 5,634,735 A * | 6/1997 | Horton | E02F 3/3613 403/321 |
| 5,643,271 A | 7/1997 | Sederholm et al. | |
| 5,720,750 A | 2/1998 | Koller et al. | |
| 5,769,853 A | 6/1998 | Quetlin | |
| 5,810,830 A | 9/1998 | Noble et al. | |
| 5,820,009 A | 10/1998 | Melling et al. | |
| 5,827,290 A | 10/1998 | Bradley | |
| 5,993,455 A | 11/1999 | Noble | |
| 6,190,416 B1 | 2/2001 | Choteau et al. | |
| 6,205,884 B1 | 3/2001 | Foley et al. | |
| 6,224,605 B1 | 5/2001 | Anderson et al. | |
| 6,238,435 B1 | 5/2001 | Meulink et al. | |
| 6,368,324 B1 | 4/2002 | Dinger | |
| 6,527,803 B1 | 3/2003 | Crozet et al. | |
| 6,537,280 B2 | 3/2003 | Dinger et al. | |
| 6,610,066 B2 | 8/2003 | Dinger et al. | |
| 6,663,636 B1 | 12/2003 | Lin | |
| 7,010,996 B2 | 3/2006 | Schick et al. | |
| 7,014,156 B2 | 3/2006 | Apezetxea et al. | |
| 7,124,479 B2 | 10/2006 | Johnson | |
| 7,322,843 B1 | 1/2008 | Lee et al. | |
| 7,325,693 B2 | 2/2008 | Bruns et al. | |
| 7,396,054 B2 | 7/2008 | Carrier | |
| 7,591,821 B2 | 9/2009 | Kleman | |
| 7,749,227 B2 | 7/2010 | Lechot et al. | |
| 7,922,726 B2 | 4/2011 | White | |
| 7,935,125 B2 | 5/2011 | Bastian et al. | |
| 7,938,679 B2 | 5/2011 | Wadsworth et al. | |
| 7,976,548 B2 | 7/2011 | Burgi et al. | |
| 8,021,365 B2 | 9/2011 | Phan | |
| 8,216,240 B2 | 7/2012 | Dewey | |
| 8,337,502 B2 | 12/2012 | Bastian et al. | |
| 2005/0234462 A1 | 10/2005 | Hershberger | |
| 2005/0234463 A1 | 10/2005 | Hershberger et al. | |
| 2006/0122701 A1 | 6/2006 | Kiester | |
| 2006/0162707 A1 | 7/2006 | Peck et al. | |
| 2007/0233134 A1 | 10/2007 | Bastian et al. | |
| 2008/0004628 A1 | 1/2008 | White | |
| 2008/0033444 A1 | 2/2008 | Bastian et al. | |
| 2008/0077241 A1 | 3/2008 | Nguyen | |
| 2008/0172061 A1 | 7/2008 | Ragbir | |
| 2008/0177265 A1 | 7/2008 | Lechot | |
| 2008/0195101 A1 | 8/2008 | Lechot et al. | |
| 2008/0255565 A1 * | 10/2008 | Fletcher | A61B 17/1659 606/80 |
| 2009/0218828 A1 * | 9/2009 | Schumacher | B60J 7/185 292/217 |
| 2010/0023016 A1 | 1/2010 | Botimer | |
| 2010/0121331 A1 | 5/2010 | Sharp et al. | |
| 2011/0160733 A1 | 6/2011 | Wallstein et al. | |
| 2011/0160734 A1 | 6/2011 | Bastian et al. | |
| 2012/0083769 A1 | 4/2012 | Burgi et al. | |

* cited by examiner

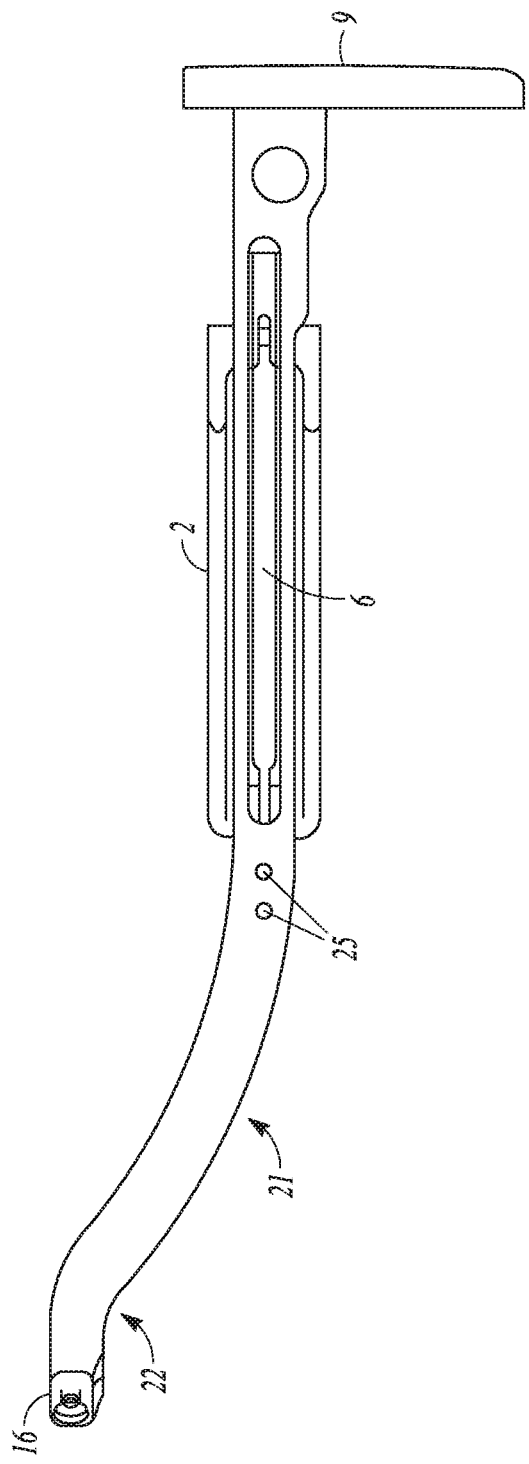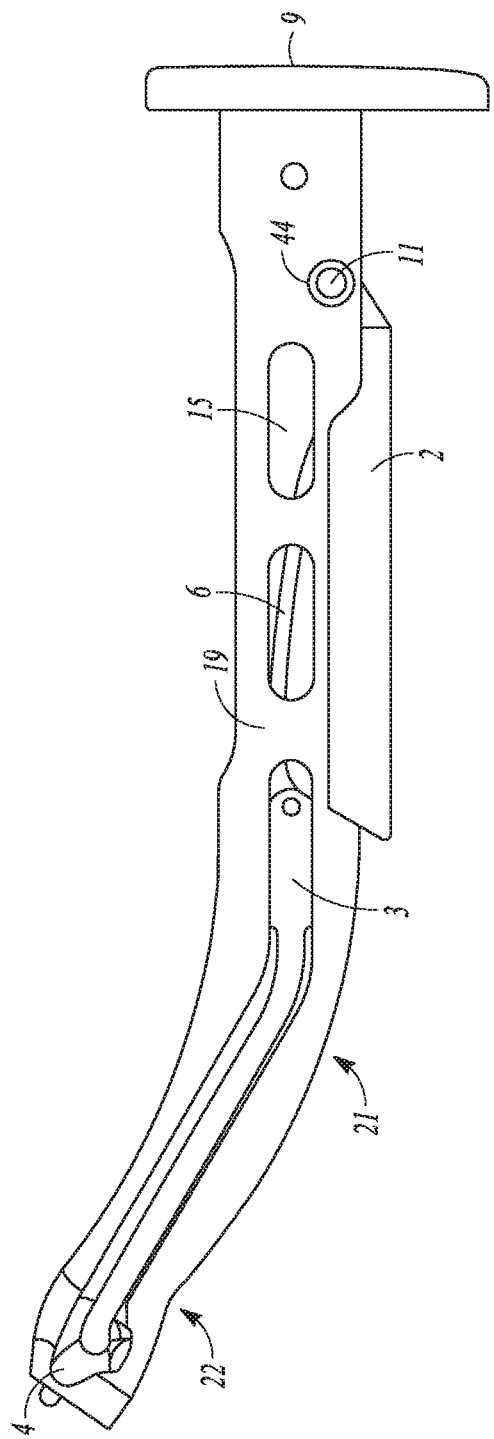

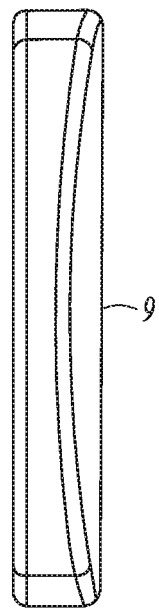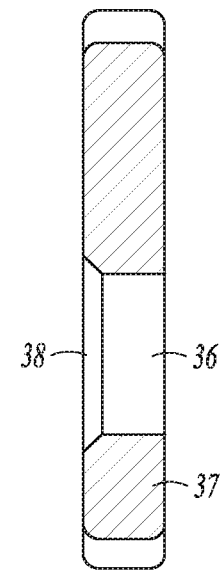
FIG. 13A          FIG. 13B

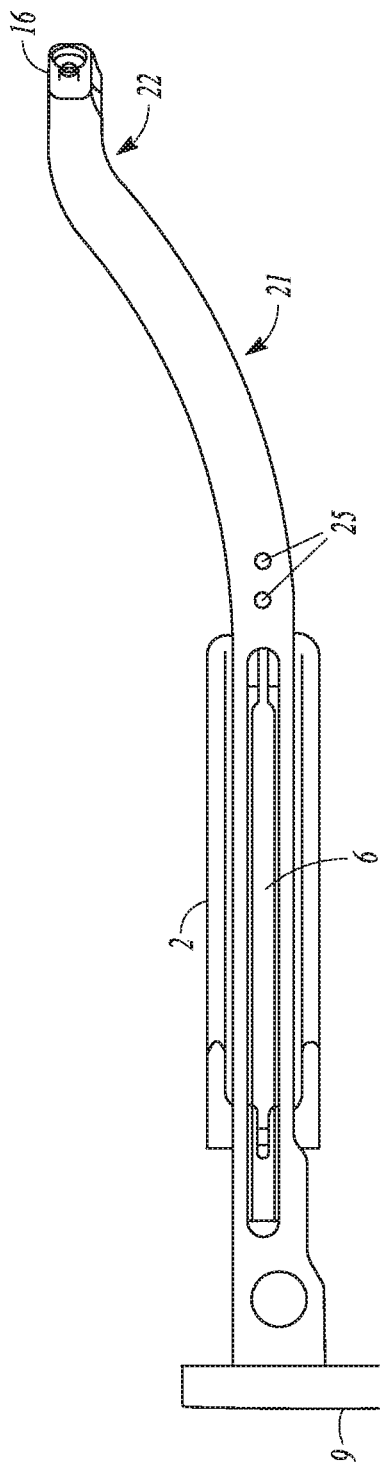
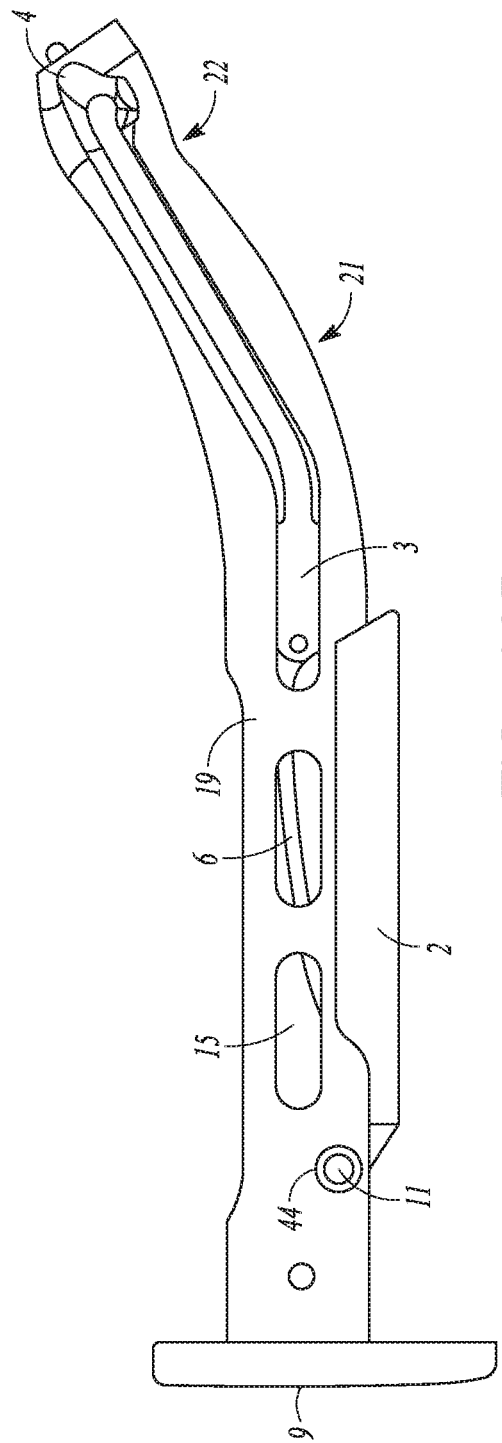
FIG. 19A
FIG. 19B

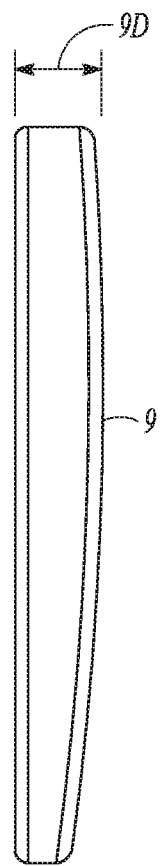
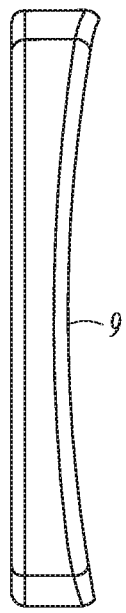
FIG. 30A
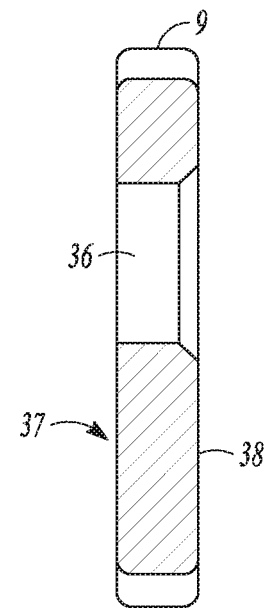
FIG. 30B

SURGICAL TOOL HANDLE ASSEMBLIES AND RELATED METHODS

RELATED APPLICATIONS

This application claims the benefit of priority of U.S. Provisional Patent Application Ser. No. 61/719,709, filed on Oct. 29, 2012, and U.S. Provisional Patent Application Ser. No. 61/800,423, filed on Mar. 15, 2013, under 35 U.S.C. § 119(e), the entire disclosures of which are expressly incorporated herein by this reference as if fully set forth herein.

TECHNICAL FIELD

This patent document pertains generally to medical equipment. More particularly, the present patent document relates to a handle assembly for use with a surgical tool.

BACKGROUND

A variety of means are used to cut or otherwise shape a portion of a bone during orthopedic surgical procedures, including, saws, knives, files, blades, broaches, reamers, rasps and similar orthopedic surgical tools. Such tools can include a handle, integral to or separately detachable from the cutting tool, for grasping the surgical tool during use and to provide leverage to perform the cutting or shaping of a bone during the orthopedic surgical procedure.

In certain surgical procedures, it can be necessary to drill or ream an intramedullary canal of a bone. For example, in the replacement of a hip joint, it can be necessary to replace a natural femoral head with a prosthetic stem affixed within a canal of the femur. The procedure for implanting the prosthetic stem can include the use of a broach or rasp in preparing the femoral shaft for reception of the prosthetic stem by providing contouring of the femoral shaft to the gross geometry of the prosthetic stem, thereby assuring accurate location and good fit. In order to facilitate utilization of such a broach or rasp tool, it can be useful to selectively detach the working portion of the tool from the handle to facilitate precise gauging of the location of the tool within the femoral shaft, to facilitate cleaning of the tool, and for other reasons.

A number of detachable handles for use with releasable tools, such as broaches or rasps, exist. However, known handles exhibit a number of problems, including a failure to achieve a tight fit between the tool and the handle, resulting in a loose coupling. Inadequate locking or a loose connection between the tool and the handle can impair control of the tool during a surgical procedure.

Handles known for use in connection with orthopedic cutting tools include, for example, those discussed in U.S. Pat. Nos. 5,190,550, 5,261,915, 5,324,293, 5,531,750, 5,643,271, 6,663,636, and U.S. Patent App. Pub. No. 2012/0083769.

OVERVIEW

The present inventors recognize, among other things, that it would be useful to have an attachable surgical tool handle that secures a surgical tool (e.g., a cutting tool) to the handle during use with greater force than existing handles, and that is readily disengaged from the surgical tool after use. The present inventors further recognize that it would be useful to have a surgical tool handle that enables a surgeon to better position a surgical tool to facilitate preparing a bone site to receive a prosthetic implant in a minimally invasive surgical procedure.

The present surgical tool handle assembly can comprise an elongated body having a frame that defines a chamber which houses a linking mechanism and a locking mechanism, and which has an opening or tool aperture and a tool receiving channel at a distal end to receive an engagement portion or a mating member of a surgical tool. The linking mechanism can include a lever and a translation bar joined in a linking arrangement by a spring. The locking mechanism can include a ramp feature, which can be formed as part of the frame and that includes a track, a part of which can define a ramp surface, and a cam that can engage the ramp surface. The ramp feature and cam can be disposed adjacent the tool receiving channel.

The linking mechanism and the locking mechanism can cooperate to create a locking moment, in which a tracking post of the translation bar engages a translation track on the cam, and a ramp post on the translation bar engages the ramp track. When the lever is in a first unlocked position, due to its relationship with the translation bar and spring, and the translation bar's corresponding relationship to the ramp feature and the cam, the unlocked position of the lever can establish a first unlocked position of the translation bar and the cam.

A mating member of a tool, such as a long post or trunnion of a surgical tool, can be inserted into the receiving channel when the handle assembly is in the unlocked position. As the lever is moved from the unlocked position to the locked position, a locking force can be created in the spring that can be translated to the translation bar in a distal direction toward the cam. The locking force of the translation bar against the cam can move the cam into locking engagement with the mating member of the surgical tool.

The angular relationship between the ramping surface of the track and the ramp post of the translation bar can provide a mechanical advantage with respect to the locking moment of the cam. The range of angles that can be used for the ramp feature with respect to the longitudinal axis of the frame can be between 10-70 degrees. The optimal angle for the ramp feature is dependent on the orientation of the cam and the connection arrangement between the translation bar and cam.

The ramp and post of the translation bar can permit control of the magnitude and direction of a normal force that contributes to the locking moment of the cam. When the lever is in a locking position, it can create a force on the spring, which is transferred to the transfer bar and from the transfer bar to the ramp, resulting in a cam locking moment and locking of the mating portion of the tool in the handle, thereby securing the tool to the handle.

To better illustrate the prosthetic handle assemblies disclosed herein, a non-limiting list of examples is provided here:

Example 1

A surgical tool handle assembly, comprising: a housing including a frame and having a proximal end and a distal end, the distal end including a receiving chamber configured to receive a mating member or feature of a surgical tool; a ramp feature adjacent the receiving channel; a cam pivotally engaged with the frame, the cam having at least one camming surface configured to engage a surface of the ramp feature, and at least one locking surface configured to lockingly engage the mating member; and an actuation assembly configured to drivingly engage the cam into locking engagement with the mating member.

Example 2

The handle assembly of Example 1, wherein the actuation assembly comprises a lever.

Example 3

The handle assembly of Example 2, wherein the lever is configured to pivotally engage, directly or indirectly, the cam to locking engagement with the mating member.

Example 4

The handle assembly of any one of Examples 2 or 3, wherein the actuation assembly further comprises a linking member pivotally engaged, directly or indirectly, with the lever.

Example 5

The handle assembly of Example 4, wherein the linking member comprises one of a translation bar and a spring.

Example 6

The handle assembly of Example 4, wherein the linking member is movably engaged with at least one of the ramp feature and the cam.

Example 7

The handle assembly of Example 6, wherein the linking member is movably engaged with the ramp and the cam.

Example 8

The handle assembly of any one of Examples 1-7, wherein the cam includes an aperture defining a cam track.

Example 9

The handle assembly of Example 8, wherein the ramp feature comprises a ramp track defining a ramping surface.

Example 10

The handle assembly of Example 9, wherein actuation assembly includes a translation bar having at least one post, and wherein the cam track is disposed to receive the at least one post.

Example 11

The handle assembly of Example 10, wherein the at least one post comprises a first post and a second post, the first post configured to engage the cam track and the second post configured to engage the ramping surface.

Example 12

A surgical tool handle assembly, comprising: a housing including a frame and having a proximal end and a distal end, the distal end including a receiving chamber configured to receive a mating member of a surgical tool; a ramp feature adjacent the receiving channel, the ramp feature including a ramp track defining a ramping surface; a cam configured to be disposed within the ramp feature and having at least one camming surface engaged with the ramping surface, the cam being pivotally engaged with the frame and having at least one locking surface configured to lockingly engage the mating member; and a lever pivotally connected to a linking mechanism, the linking mechanism configured to simultaneously engage the cam and the ramping surface to drivingly engage the cam into locking engagement with the mating member.

Example 13

A method of locking a surgical tool to a tool handle assembly, comprising: providing or obtaining a tool handle assembly, the handle assembly including, a body defining a receiving channel configured to receiving a mating end of a surgical tool and a ramp feature; a locking cam pivotally engaged with the ramp feature; a cam locking bar and a lever, wherein a proximal end of the cam locking bar is engaged with the lever, and a distal end of the cam locking bar is engage with each of the ramp feature and the locking cam; inserting a mating member of a surgical tool into the receiving channel; and moving the lever from a first unlocked position to a second locked position, including displacing the cam locking bar to drive the cam into locking engagement with the mating member of the surgical tool.

These and other examples and features of the present surgical instrument handle and related kits and methods are set forth in part in the following Detailed Description. This Overview is intended to provide non-limiting examples of the present subject matter—it is not intended to provide an exclusive or exhaustive explanation. The Detailed Description below is included to provide further information about the present surgical instrument handle and related kits and methods.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings.

In the drawings, like numerals can be used to describe similar elements throughout the several views. Like numerals having different letter suffixes can be used to represent different views or features of similar elements. The drawings illustrate generally, by way of example, but not by way of limitation, various embodiments discussed in the present document.

FIGS. 2A, B illustrate respective bottom and side views of a right tool handle, as constructed in accordance with at least one embodiment.

FIGS. 13A, B illustrate a side view, and a cross-sectional view through section A-A of FIG. 11, of a right strike plate as constructed in accordance with at least one embodiment.

FIGS. 19A, B illustrate respective bottom and side views of a left tool handle, as constructed in accordance with at least one embodiment.

FIGS. 30A, B illustrate a side view, and a cross-sectional view through section A-A of FIG. 28, of a left strike plate as constructed in accordance with at least one embodiment.

DETAILED DESCRIPTION

Figure 1:
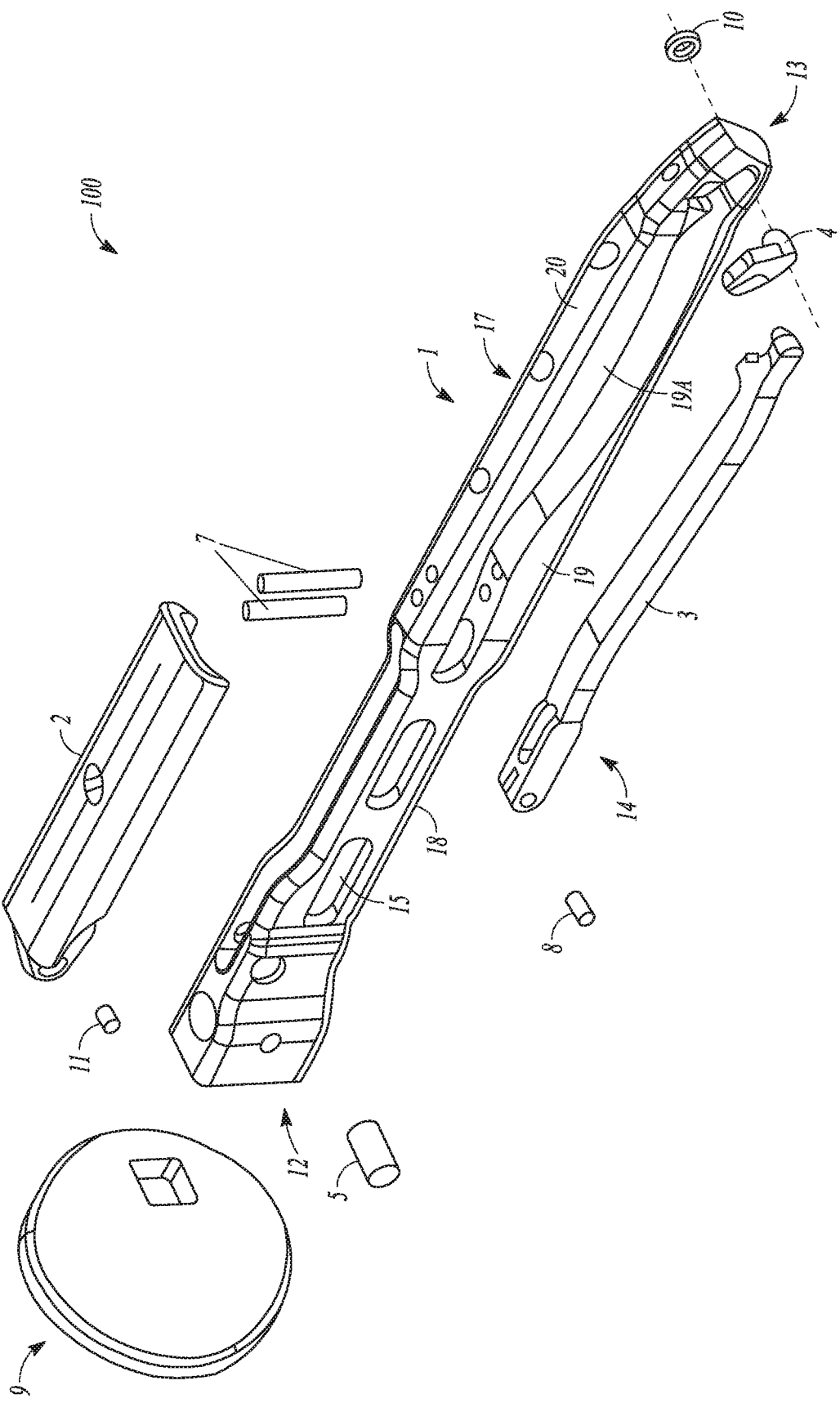
FIG. 1 illustrates an exploded isometric view of a surgical right tool handle, as constructed in accordance with at least one embodiment.

FIGS. 1 through 40 illustrate surgical tool handle assemblies, as constructed in accordance with the present invention. A tool handle assembly can be releasably connected to a surgical tool, such as a broach or rasp (not shown) for performing a minimally invasive orthopedic surgery. Other tools that can be used with the handle assembly include, but are not limited to, awls, reamers, angled drivers, twist drills, flexible drills, cannulated drills, bayonet drills, bayonet taps, drill guides, adjustable angle drill guides, taps, and cannulated taps.

In the figures, embodiments may illustrate features with a "handedness" or with a neutral configuration (without a handedness). Handedness of any feature disclosed herein should not be understood to require that such feature have any handedness, and all features are deemed to include a neutral configuration, in additional to any particular or alternate handedness that may be disclosed herein or illustrated in any one or more of the figures. In this disclosure, like numerals refer to the same feature or component of a right tool handle assembly and left tool handle assembly without separate reference to the right-handedness or left-handedness (or neutrality) of the component in any one or more embodiments. Generally, reference to the handedness of a particular component is not necessary for an understanding of the invention, however, where reference to the handedness of a feature or component in one or more embodiments is useful, such feature or component can be designated by the applicable reference numeral and the letter "R" for right-handed components and by the reference numeral and the letter "L" for left-handed components.

Throughout this disclosure, reference to a "right" or "left" to a handle assembly component or a handle assembly, refers to a directional feature of the tool handle assembly or component. For example, whether the features of the tool handle assembly are disposed or configured for preferential use with respect to a particular side of a body, e.g., a body part disposed on a right side or left side of a body, or a right femur or a left femur (with respect to a human body, sidedness being viewed from the patient perspective).

Right-handedness or left-handedness can alternatively or additionally correspond to one or more directional offsets or curves within a region of the tool handle assembly, for example in certain embodiments one ore more curves adjacent a distal end (surgical tool mating end) can cause a distal end of the tool handle assembly to be offset at an angle in relation to a longitudinal axis of a proximal end of the tool handle assembly. The offset angle can be an angle to facilitate preferential use on a particular side of a human body, as disclosed above, or may facilitate a particular surgical approach or accommodate specific anatomical features that may impede access to a desired surgical site.

Figure 17:
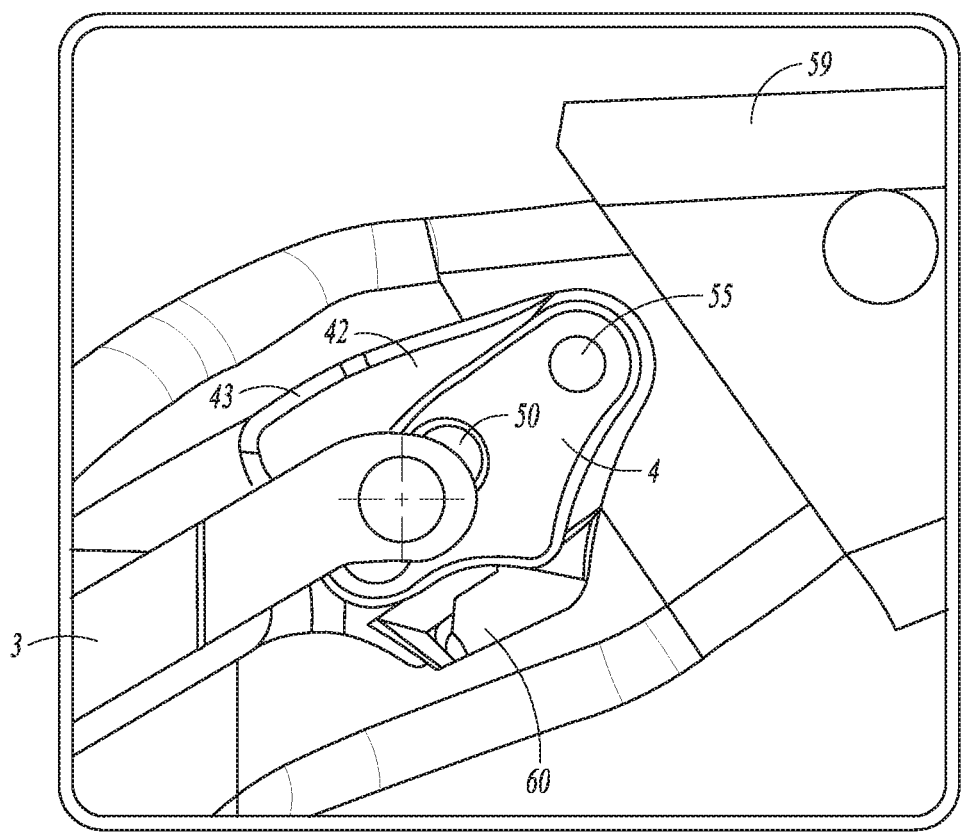
FIG. 17 illustrates a view of a cam locking moment, a transfer bar engaged with a cam, and the cam engaged with a ramp of a frame and in locking relation to an engagement portion of a cutting tool, as constructed in accordance with at least one embodiment.

As illustrated, for example, in FIGS. 1, 2A-B, 3A-C, 5, 18, 19A-B, 20A-C, and 40, an embodiment of a tool handle assembly 100, 200 can comprise an elongated body 1 having a proximal end 12, a distal end 13 and an intermediate translation region 14 extending between proximal end 12 and distal end 13. Proximal end 12 of body 1 can be configured for gripping during use and can optionally be configured to receive strike plate 9 for striking with an impacting tool. Distal end 13 of body 1 can be configured to engage a mating member 60 of a surgical tool head 59 (as shown in FIG. 17). For example, in an embodiment distal end 13 of body 1 can include an aperture 40 opening into receiving chamber 41 configured to receive mating member 60. Body 1 comprises a frame that defines one or more translation chambers 15 configured to house one or more components of a linking mechanism and/or a locking mechanism.

In one embodiment, a linking mechanism can comprise a lever 2 pivotally connected to the frame of body 1, for example, lever can be pivotally connected to body 1 by pivot pin 5, 7, 8, 11. As best illustrated in FIGS. 1, 2A-B, 3A-C, 18, 19A-B, 20A-C, 21A-B, 34A-C, and 35A-B, an embodiment of lever 2 can be configured to rest or seat on a top surface 17 of body 1 when lever 2 is in a locking position. In one embodiment, lever 2 is configured to seat over a portion of translation chamber 15 adjacent a proximal end 12 of the tool handle assembly 100, 200. Lever 2 can include a top portion 28, first and second side portions 29 (respectively, first side portion and second side portion 29A, 29B), a pivot end 30, and a lever front edge 31 which can be angled with respect to lever top portion 28. Top portion 28, first and second side portion 29A, 29B define a general U-shaped configured such that a portion of body 1 can be received into lever 2.

Lever top portion 28 can be configured to rest or seat on the top surface 17 of body 1, while first and second side portion 29A, 29B can be configured to be disposed adjacent opposite sides of intermediate translation portion 14 of body 1 when lever 2 is in a locking position. In an alternate embodiment, lever 2 can be configured such that lever pivot end 30, disposed opposite lever front edge 31 is seated within a translational chamber 15, 19A of body 1 to permit pivotal engagement of the lever 2 simultaneously with body 1 and linking member 3, 6 disposed within translational chamber 15. In an embodiment, lever pivot end 30 can be curved at a chamber-facing surface 30C to prevent impinging the pivotal movement of lever 2 about its full range of motion.

As best illustrated in FIGS. 2B, 3B, 19B, 20B, 34A-C, and 35A-B, the lever 2 can be pivotally engaged with the body 1 at pivot hole 44 disposed in body 1, and lever pivot hole 27. In an embodiment, body pivot hole 44 can be disposed adjacent proximal end 12 of the body 1 and can be configured to be pivotally engaged with the lever pivot hole 27, such that the lever 2 pivots in relation to the body 1 when the two are engaged by a hinge pin 11. The lever pivot end 30 can comprise a bifurcated end with portions 30A, 30B (see FIG. 35B). The lever pivot end 30 can also include a second pivot hole 26 for pivotal engagement of the lever 2 with another linking mechanism component, such as a spring 6 or a translation bar 3.

Figure 3A:
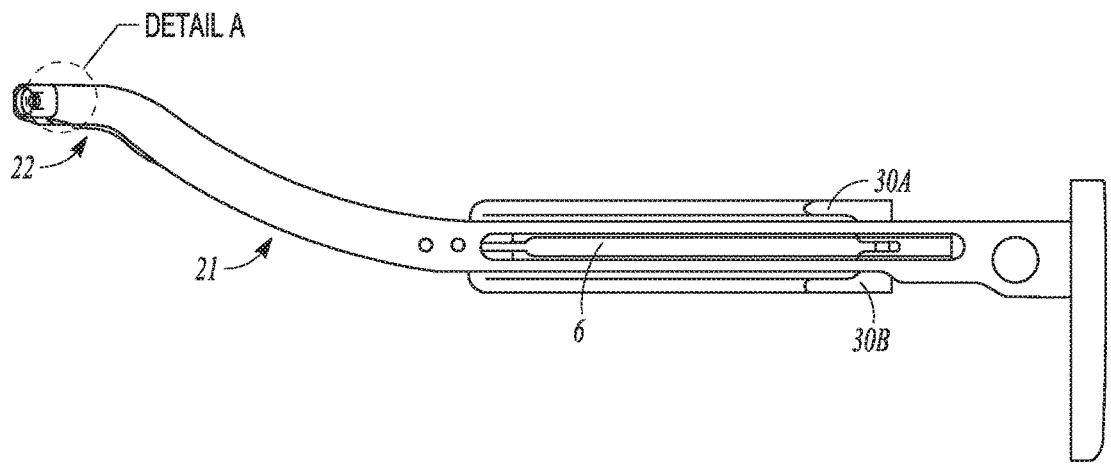
FIGS. 3A, B, C illustrate respective bottom, side, and top views of a right tool handle, as constructed in accordance with at least one embodiment.
Figure 3B:
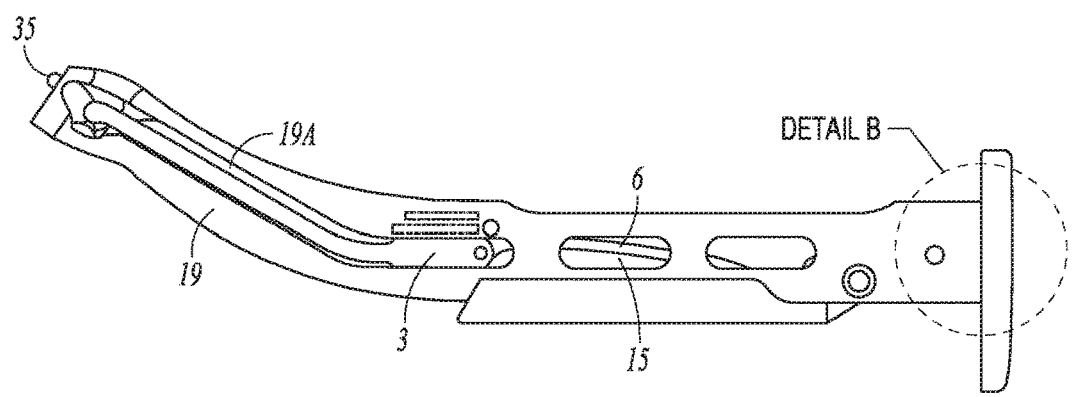
Figure 3C:
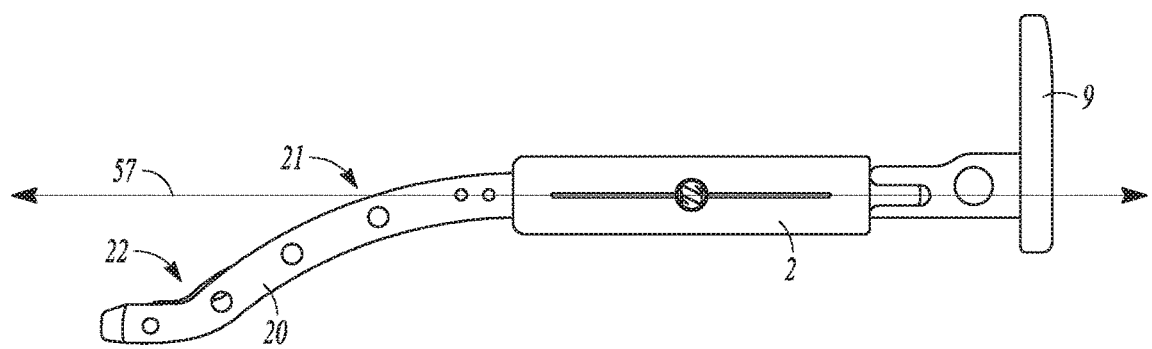
Figure 4A:
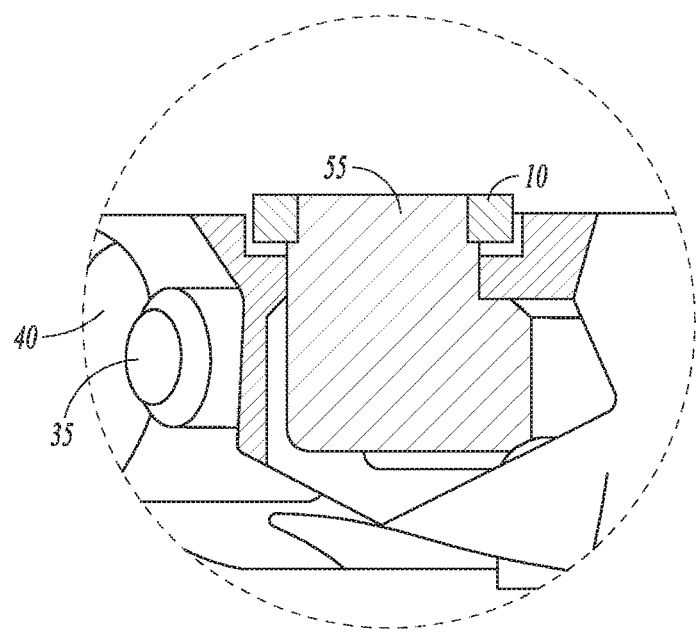
FIGS. 4A, B illustrate detailed views of section A of FIG. 3A, and section B of FIG. 3B.
Figure 4B:
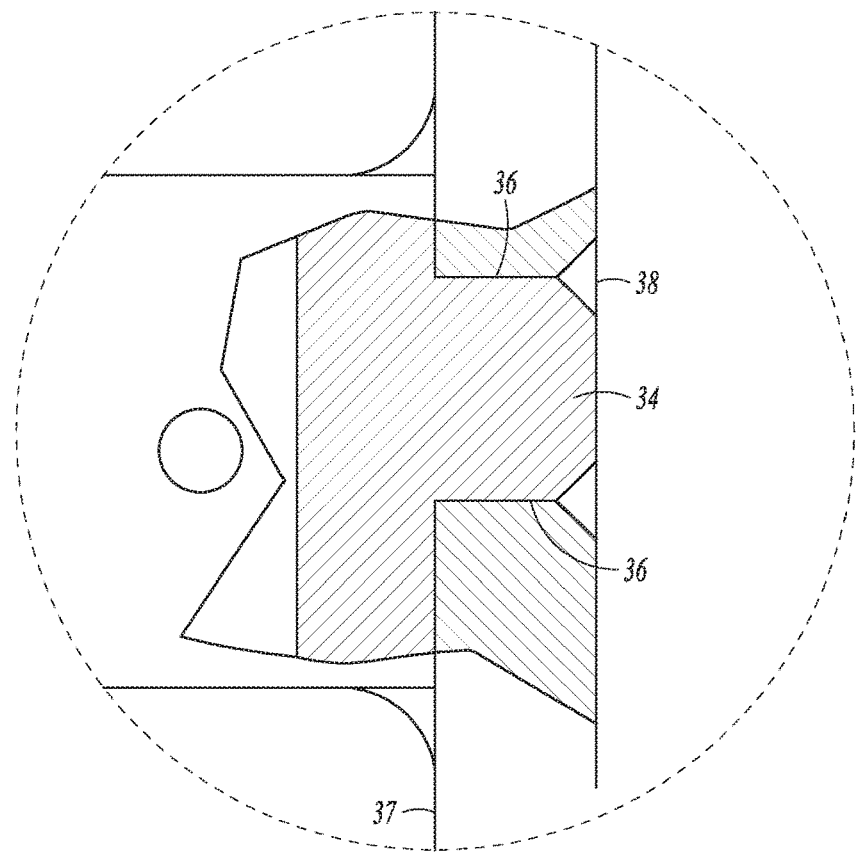

In an embodiment, lever 2 can be pivotally engaged with a linking component to provide a linking mechanism for translation of a force generated by lever 2. By this linking arrangement, a force generated adjacent proximal end 12 by lever 2 moving from an unlocked position to a locked position, in which lever 2 rests or is seated on frame of body 1 (for example, as illustrated in FIGS. 3A-C), can be translated through other components of a linking mechanisms (e.g., spring 6 and/or the translation bar 3) to a locking mechanism disposed at distal end 13 of tool handle body 1, translating the force into a locking force for locking a mating member 60 of a tool head 59, as more fully discussed below.

In an embodiment, linking mechanism can comprise lever 2 in linking arrangement with translation bar 3 through pivotal connection, such as through a hinge or pivot pin 5, 8, 11. In an alternate embodiment, lever 2 and translation bar 3 can be in linking arrangement with an elastic member or spring 6 disposed between lever 2 and translation bar 3. In certain embodiments, lever 2, specifically at the pivot hole 26, can be pivotally engaged with a first linking member. In one embodiment, first linking member is translation bar 3. In an alternate embodiment, first linking member is spring 6.

Figure 18:
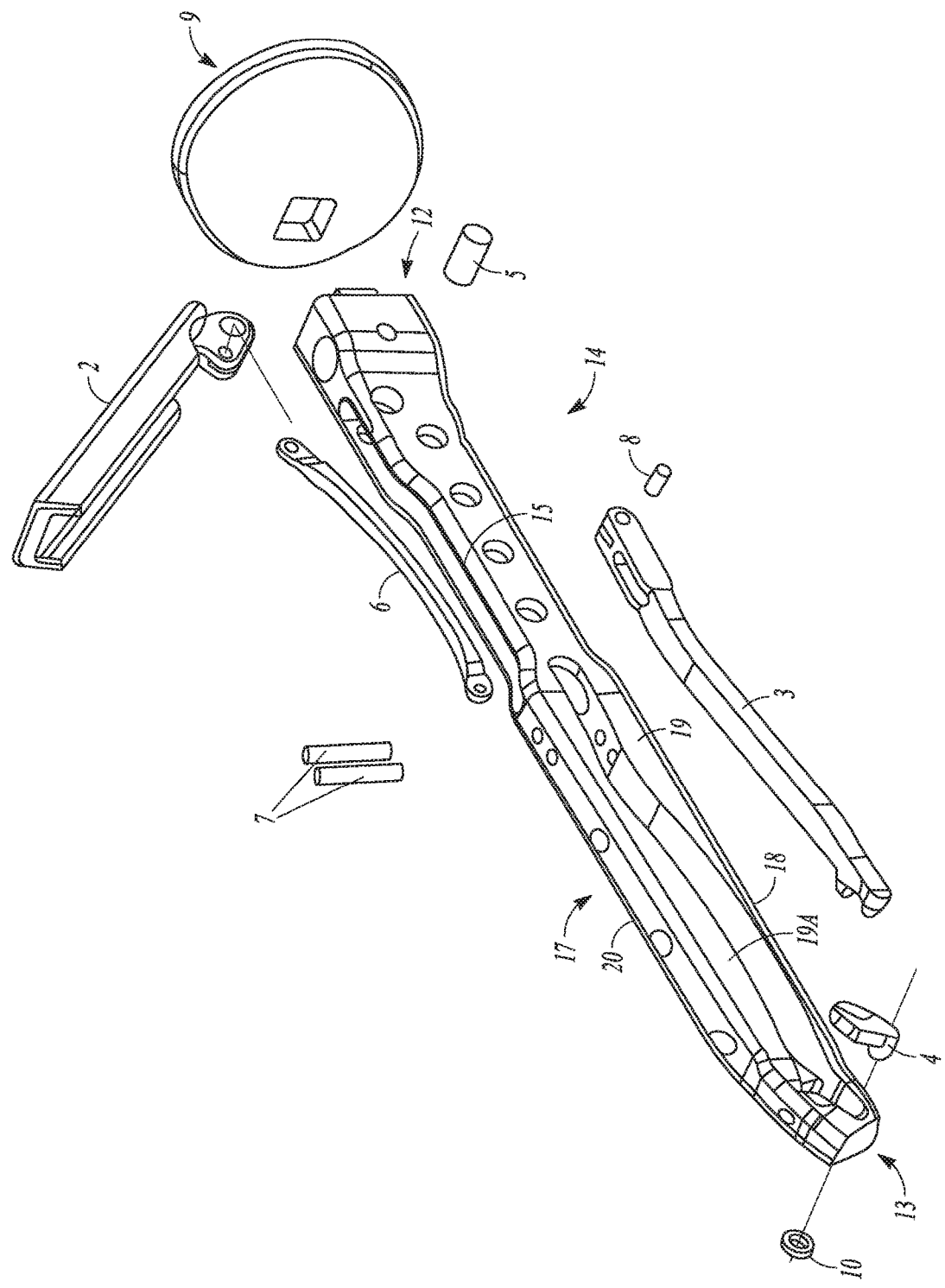
FIG. 18 illustrates an exploded view of a left handle assembly, as constructed in accordance with at least one embodiment.

In one embodiment, pivot end 3a of translation bar 3 can be pivotally engaged at pivot hole 47 with lever 2 at pivot hole 26. In an alternate embodiment, a first end 6A of spring 6 at the spring pivot hole 32 (best seen in FIGS. 36A, 36B), can be pivotally connected to lever 2 at pivot hole 26 by a pivot pin 5 (best seen in FIGS. 1, 18). In embodiment having spring 6, a second end 6B of spring 6 can be pivotally engaged to a first end 3a of translation bar 3 by pivot pin 8 (best seen in FIGS. 36A, 36B). In one embodiment, translation bar 3 can be secured within translational chamber 15, 19A by one or more long pins 7 (as best seen in FIGS. 1 and 18).

In an embodiment, spring 6 can comprise a generally curved or arcuate portion 6C. In an alternate embodiment, spring 6 can be positioned such that a curve or an arcuate portion 6c is disposed within translation chamber 15 such that spring 6 curves or arches away from a top side or top surface 17 of body 1. In another embodiment, spring 6 can configured such that a curve or arcuate portion 6 is disposed within translation chamber 15 such that it curves or arches away from a bottom side or a bottom surface 18 of body 1. In an alternate embodiment, spring 6 can include a leaf spring.

Referring to FIGS. 7, 8, 17, 24 and 25, distal end 13 of the tool handle assembly 100, 200 can be configured to provide engagement of a linking mechanism and locking mechanism for locking engagement of a mating member 60 disposed within a receiving chamber 41 disposed at distal end 13 the tool handle assembly 100, 200. In an embodiment, distal end 13 of body 1 frame can form a nose 16 which is configured to define receiving chamber 41 and is further configured to house a locking mechanism adjacent receiving chamber 41. In one embodiment, receiving chamber 41 is in communication with locking mechanism.

As best illustrated in FIGS. 15, 16A-B, 32, and 33A-B, in an embodiment locking mechanism can include a cam 4. In one embodiment cam 4 cam be pivotally engaged with distal end 13 of body 1 and linking mechanism for locking engagement of mating member 59 when it is disposed in receiving chamber 41 and lever 2 is disposed in a locked position.

Cam 4 can comprise a generally planar body having a front surface 51, a back surface 52 opposite the front surface 51, and peripheral shape. In an embodiment, peripheral shape of the cam 4 may be any shape, preferably a generally circular, oval or ovoid shape. In an embodiment, cam 4 can have a first pivot end 70 and a second tracking end 71. In one embodiment, cam 4 can comprise a projection or locking feature 72 disposed between cam pivot end 70 and cam tracking end 71 and configured to define a locking region of cam for locking engagement of mating member 60 of tool head 59. In still another embodiment, a locking surface or locking edge 54 can be disposed between cam locking feature 72 and cam tracking end 71. In one embedment, locking feature 72 is configured to provide a greater surface area for locking edge 54 to engage mating member 60. Cam 4 can include a post or shaft 55 (best seen in FIGS. 1, 16B, 18 and 33B) projecting from cam back surface 52. Cam shaft 55 is configured to pivotally engage body 1 at cam pivot hole 53 formed at distal end 13. Cam 4 can be secured to the body 1 at cam pivot hole 53 by a washer 10.

Figure 20A:
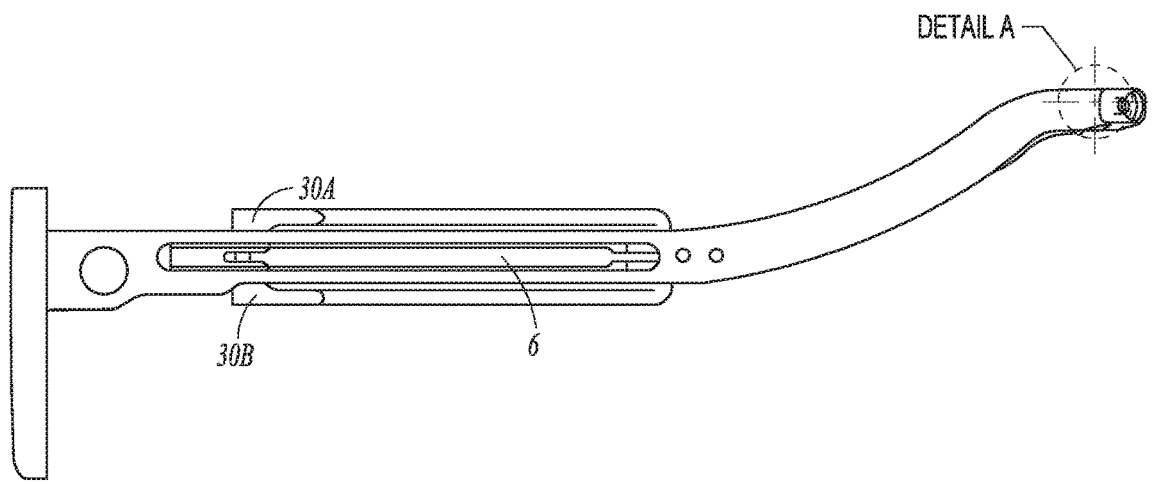
FIGS. 20A, B, C illustrate respective bottom, side, and top views of a left tool handle, as constructed in accordance with at least one embodiment.
Figure 20B:
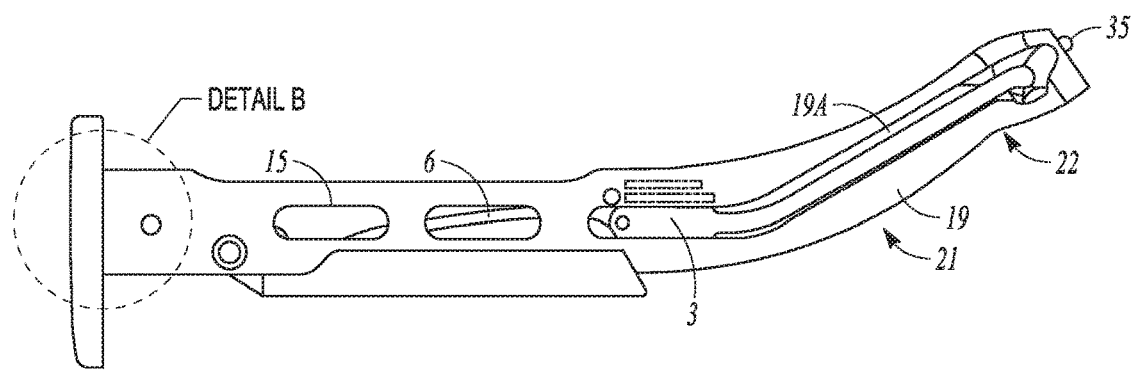
Figure 20C:
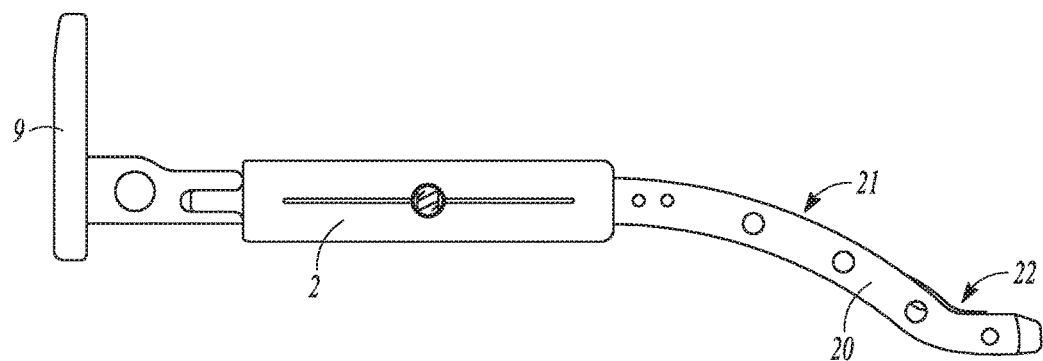
Figure 21A:
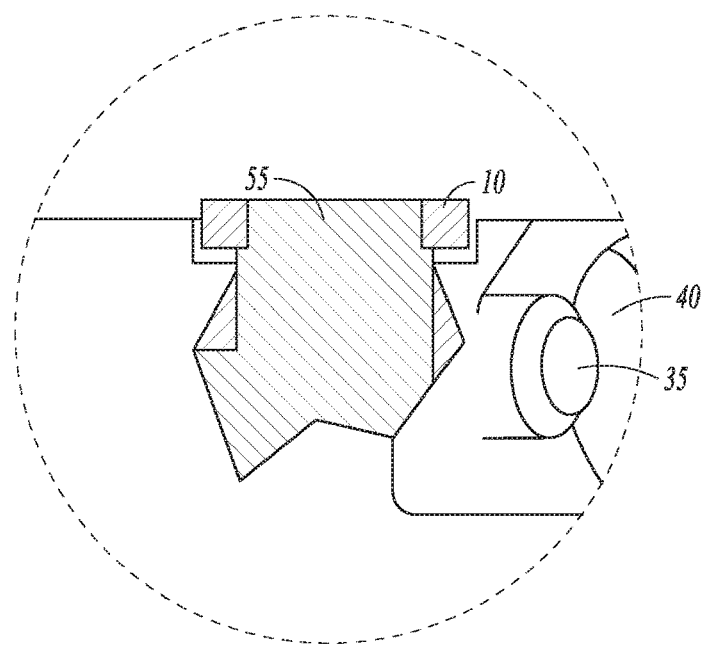
FIG. 21A, B illustrate detailed views of section A of FIG. 20A, and section B of FIG. 20B.
Figure 21B:
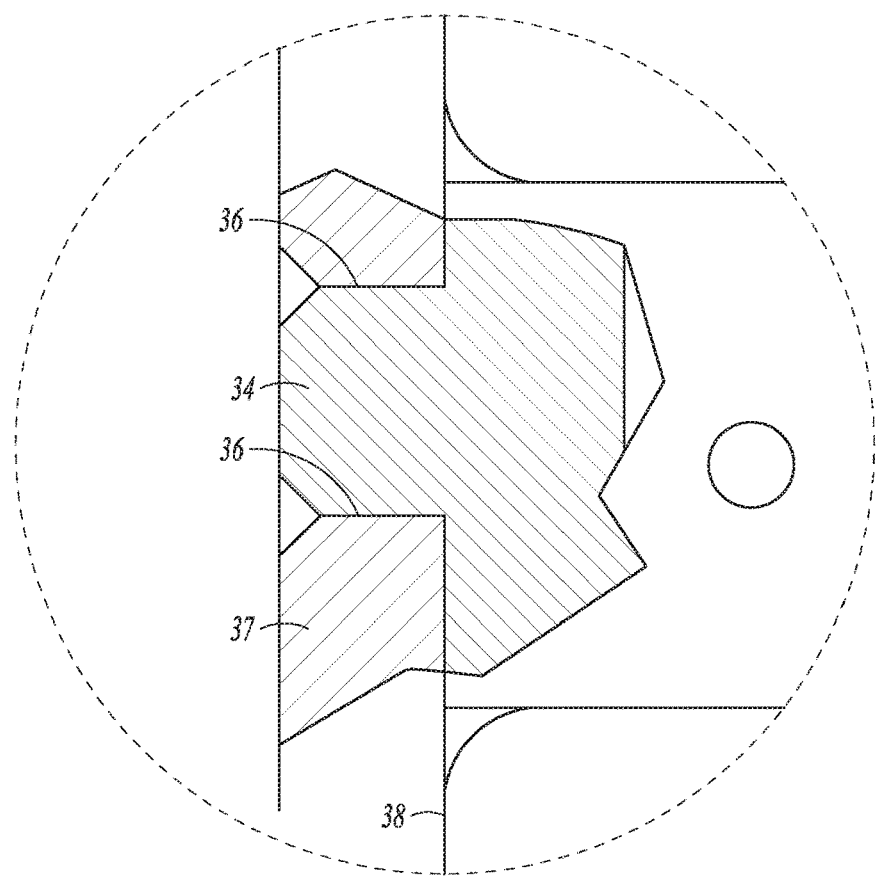

In one embodiment, cam 4 front surface 51 is configured to receive and engage translation bar 3 (in FIGS. 3B and 20B, as see through frame opening 19A). As illustrated in FIGS. 15, 16A, 17, 32, and 33A, cam 4 can have a aperture defining a cam track 50 configured to receive a track post 45 disposed on translation bar 3 (seen in FIGS. 1, 14B, 18, and 31A). The cam track can be any shape suitable for providing translational engagement between translation bar 3 and cam 4, preferably circular, oval or ovoid shaped.

As shown in FIGS. 6A, 7, 8, 17, 23A, 24, 25, in one embodiment, nose 16 includes a ramp feature 42 comprising a ramp track 43 which defines a ramp surface 43S. Ramp feature 42 is disposed within nose 16, adjacent channel 41. The ramp surface 4243S can be configured to engage a back surface 52 of cam 4. The ramp track 43 can be generally shaped to receive cam 4. In some embodiments, ramp track 43 is configured to engage at least one surface of cam 4, as illustrated in FIG. 17. In one embodiment, cam 4 can engage ramp track 43 on a cam surface that is at or adjacent to cam track end 71. In another embodiment, cam 4 can engage ramp track 43 on a cam surface that is at or adjacent to cam pivot end 70. In one embodiment, ramp feature 42 can comprise a generally rounded triangular or generally rounded arrowhead shape, having an apex adjacent mating post 35 (for example as seen on FIGS. 3B, 4A, 7, 8, 10B), and defining ramp track 43. Mating post 35 is configured to mate with a correspondingly disposed and configured aperture, chamber or channel on tool head 59 to further secure tool head 59 to distal end 13 of tool handle assembly 100, 200.

As illustrated, for example in FIGS. 1, 14B, 18, and 31A, translation bar 3 can comprise one ore more features configured to engage the locking mechanism, facilitating the locking engagement of the mating member 59 in the receiving chamber 41. In an embodiment, translation bar 3 can include a track post 45 configured to engage the cam track 50, and a ramp post 46 configured to engage the ramp track 43. In alternate embodiments, one or both of the engagements between track post 45 and cam track 50, or between ramp post 46 and ramp track 43, may be a moveable engagement, such as a sliding engagement or a pivotal engagement.

As illustrated in FIG. 17, the transfer bar 3 can be engaged with the cam track 50 allowing translation of a force (F1) against a surface of ramp track 43 causing cam 4 to move into a locked position in which a locking edge 54 engages mating member 60 of tool head 59.

The above described embodiments of tool handle assembly 100, 200, can be used to implement a method of locking a surgical tool to the tool handle assembly. When the lever 2 is in unlocked position disposed at an angle away from top surface 17 of tool handle assembly 100, 200, preferably at an angle between 0° and approximately 90°, the cam 4 can be in corresponding unlocked position (not shown). A mating member 60 of the surgical tool head 59, for example a long post or a trunnion, can be inserted into the receiving aperture 40 and seated in the receiving chamber 41 when the tool handle assembly is in the unlocked position. As the lever 2 is moved from an unlocked position into the locking position, lever 2 becomes essentially coplanar with tool handle assembly top surface 17. As lever 2 is moved into locking position, a force can be created in the spring 6 and can be translated to the translation bar 3 in distal direction toward the cam 4. A corresponding translation force (F1) of the translation bar 3 against a face of the ramp feature 42 and the ramp track 43 can cause a cam locking moment in which the cam 4 is moved a distance (D1), and the locking edge 54 engages the mating member 60 of the surgical tool head 59, thereby locking tool head 59 to tool handle assembly 100, 200.

The angular relationship between the ramp channel 43 and the ramp post 46 of the translation bar 3 can provide a mechanical advantage with respect to the locking moment of the cam. The ramp channel 43 and the ramp post 46 of the translation bar 3 can permit control of the magnitude and direction of the normal force (N) (which is the force coming off the face of the ramp feature at 90°), that contributes to the locking moment of the cam 4. The range of angles that can be used for the ramp feature with respect to the longitudinal axis 57 of the frame can range between 10° and 70°, inclusive. The optimal angle for the ramp feature 42 can be dependent upon the orientation of the cam 4 and the connection arrangement between the translation bar 3 and the cam 4, and can be determined by one of ordinary skill in the art according to conventional means and without undue experimentation.

In an embodiment, the body 1 frame can include a receiving arm 19 and an engaging arm 20. The receiving arm 19 and the engaging arm 20 can cooperate to form an intermediate translation region 14 and a distal end 13 the body 1. The receiving arm 19 and the engaging arm 20 can be joined at a nose 16 at the distal end 13 of the body (best seen in FIGS. 5, 9A, 22 and 26A). The top side 17, the bottom side 18, the receiving arm 19, and the engaging arm 20 can cooperate to define a translation chamber 15, 19A. In one embodiment, translation chamber 15 is disposed within the intermediate translational region 14 of the body 1. The translation chamber 15, 19A can be configured to receive and a house linking mechanism components as discussed above.

In an embodiment of the above-described tool handle assembly 100, 200, the tool handle body 1 may further comprise one or more curves or angles disposed between a proximal end 12 and distal end 13 of tool handle assembly 100, 200. As discussed above, a curve or angle may be beneficial for a tool handle assembly to preferentially be used on a particular side of a patient's body, or to provide a preferential access or approach to a patient's body. Referring to FIGS. 2A, 2B, 3A, 3B, and 3C, various embodiments of a double-offset right tool handle 100 are illustrated. Corresponding embodiments of a double-offset left tool handle 200 are illustrated in FIGS. 19A, 19B, 20A, 20B, and 20C. A first, horizontal offset 23 is illustrated in FIGS. 2A, 3A, and 3C (23R) and 19A, 20A, and 20C (23L). The horizontal offset can comprise an angle or offset with respect to a longitudinal axis 57 at or near a proximal end 12, and in relation to strike plate 9 affixed at the proximal end 12 of body 1. A second, vertical offset 24 is illustrated in FIGS. 2B and 3B (24R) and FIGS. 19B and 20B (24L).

Figure 5:
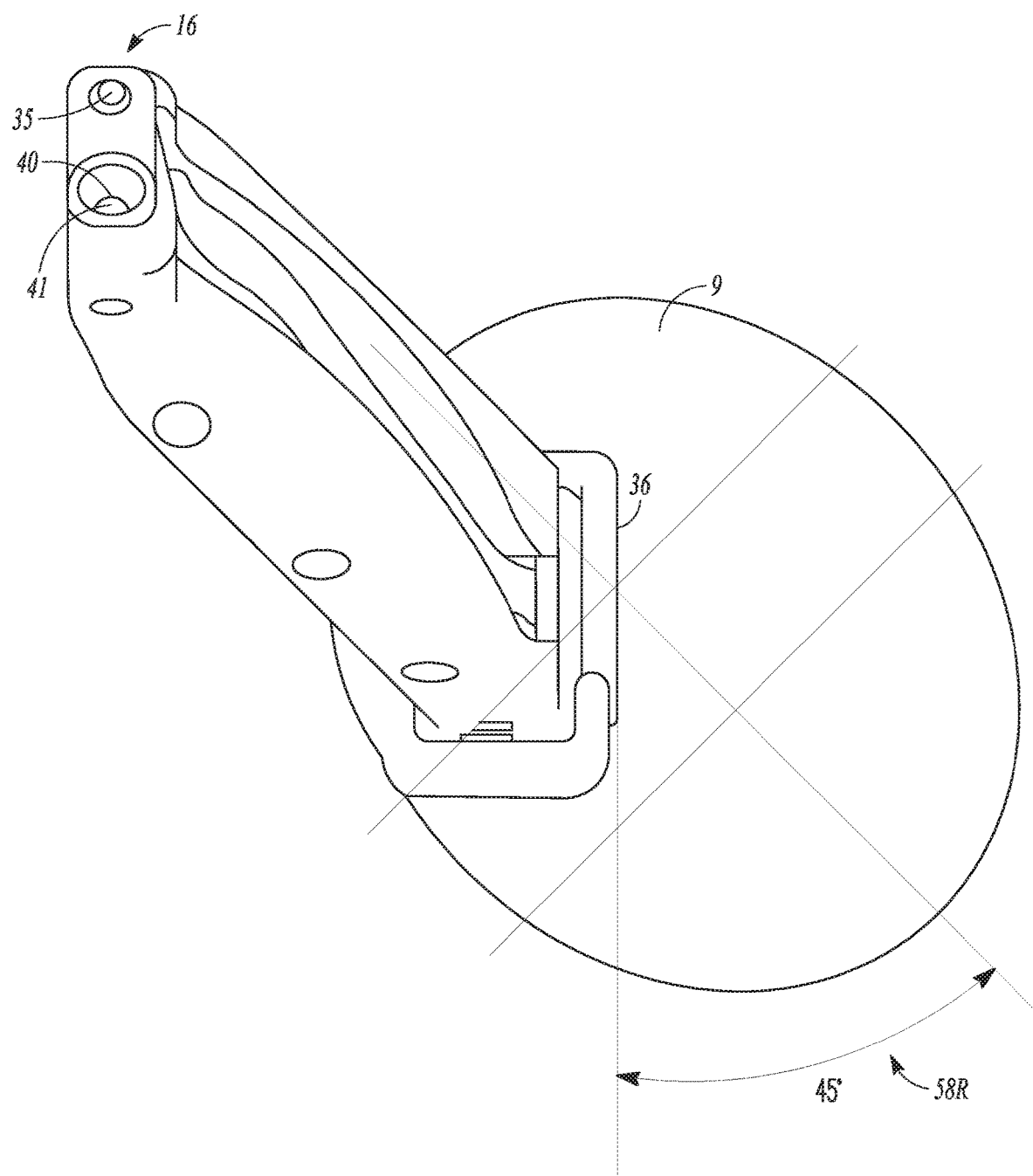
FIG. 5 illustrates an isometric view of a right tool handle, as constructed in accordance with at least one embodiment.
Figure 6A:
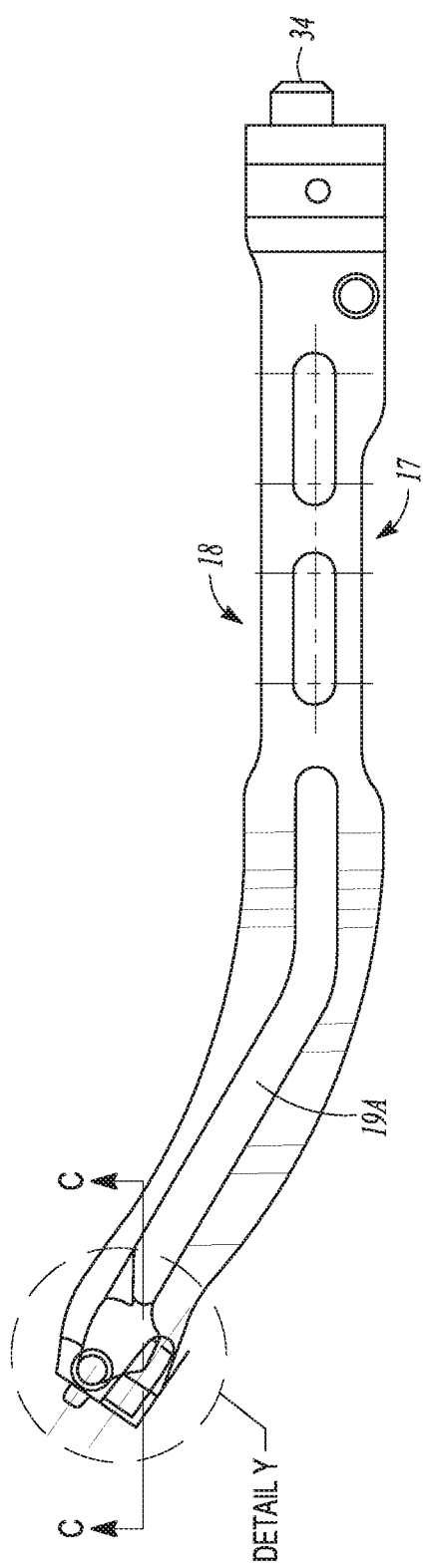
FIGS. 6A, B illustrate side views of a frame of a right tool handle, as constructed in accordance with at least one embodiment.
Figure 6B:
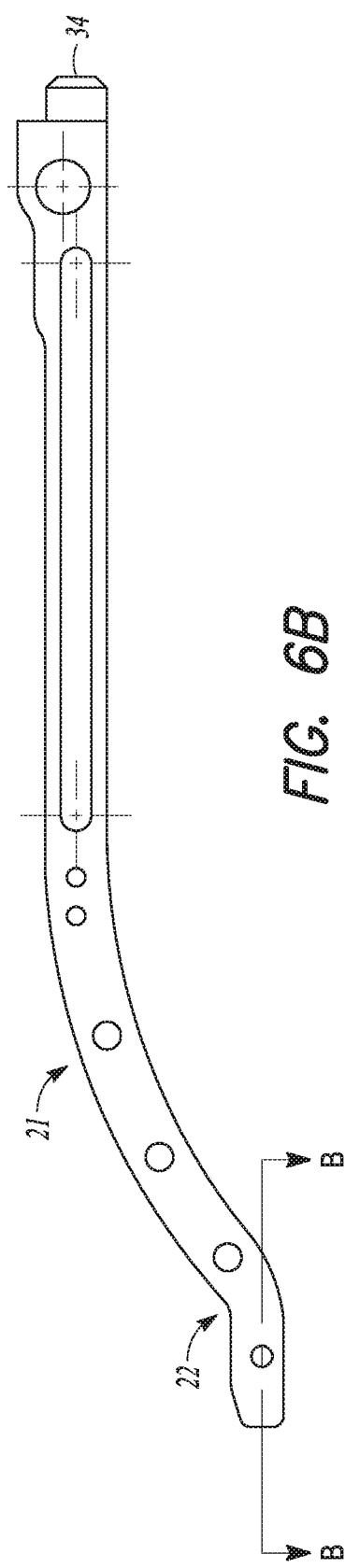
Figure 7:
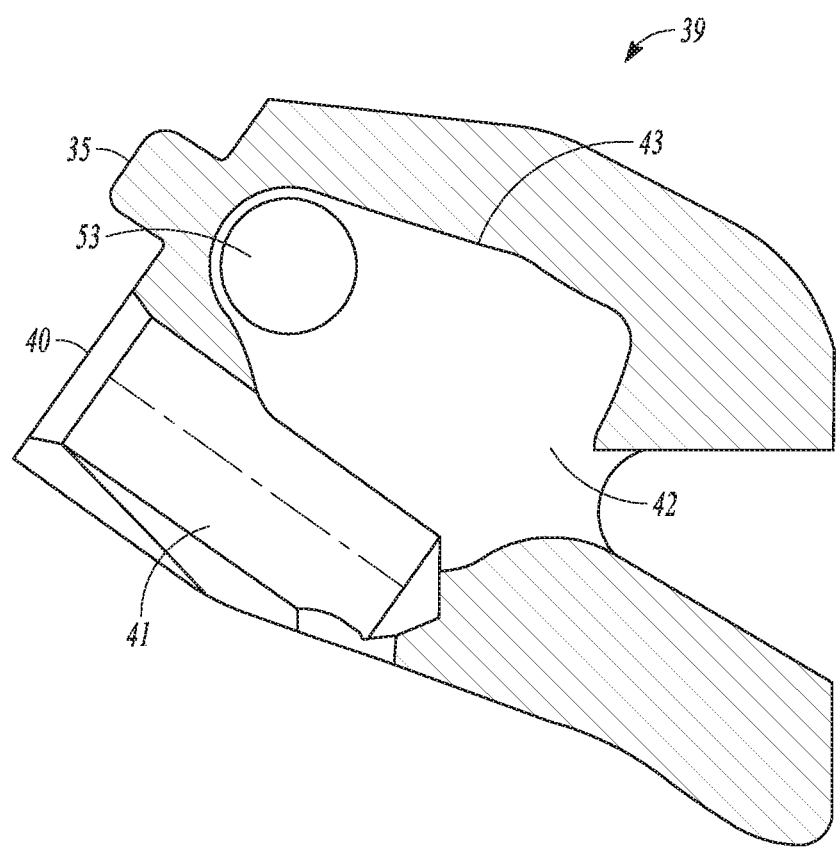
FIG. 7 illustrates a detailed view of section B-B of FIG. 6B.
Figure 8:
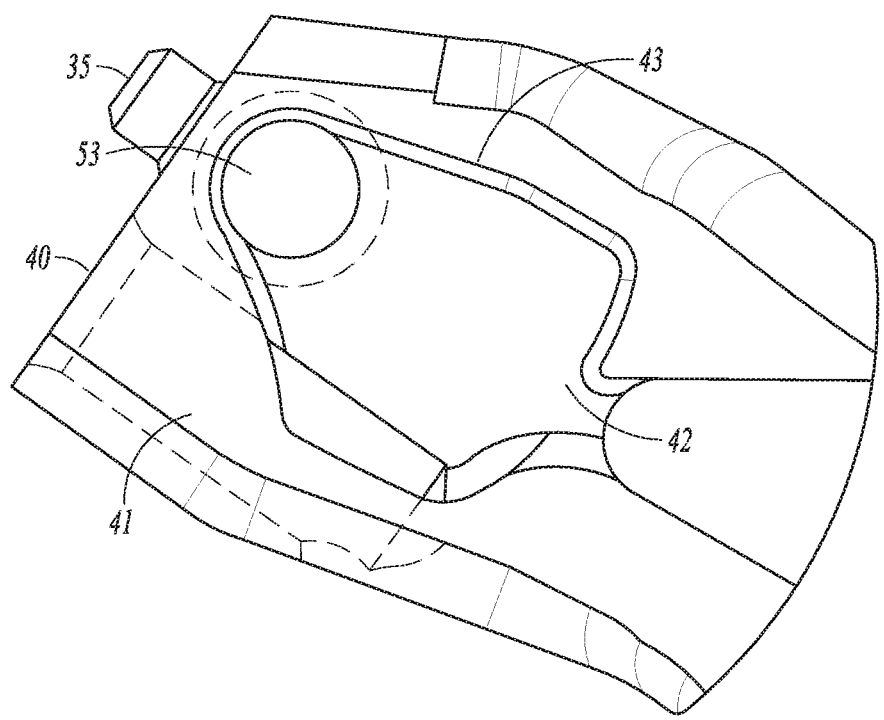
FIG. 8 illustrates a detailed view of section Y of FIG. 6A.
Figure 9A:
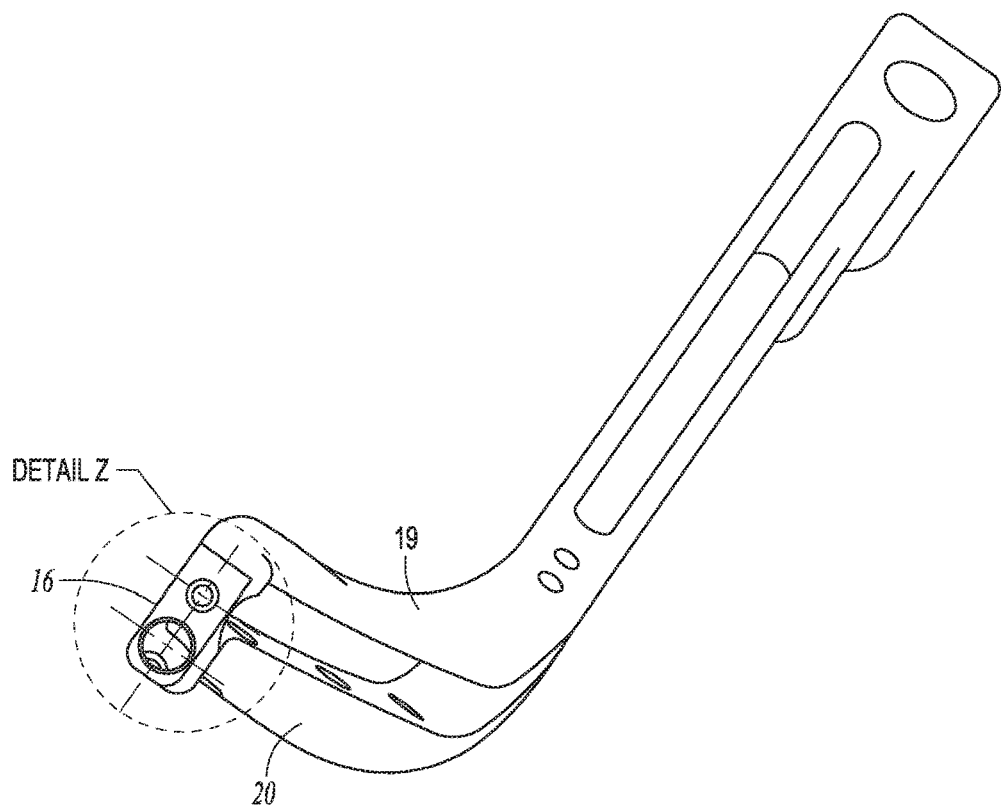
FIGS. 9A, B illustrate isometric views of a frame of a right tool handle, as constructed in accordance with at least one embodiment.
Figure 9B:
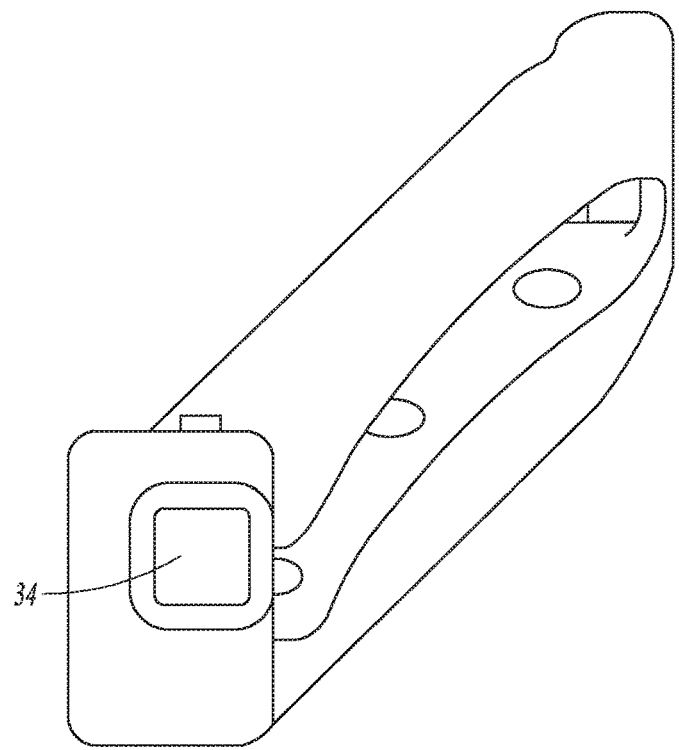
Figure 10A:
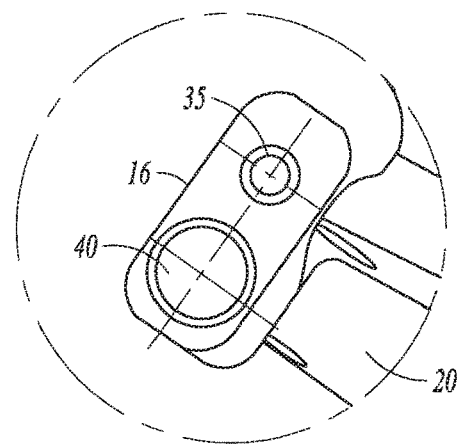
FIGS. 10A, B, C illustrate detailed views of section Z of FIG. 9A, and section C-C of FIG. 6A.
Figure 10B:
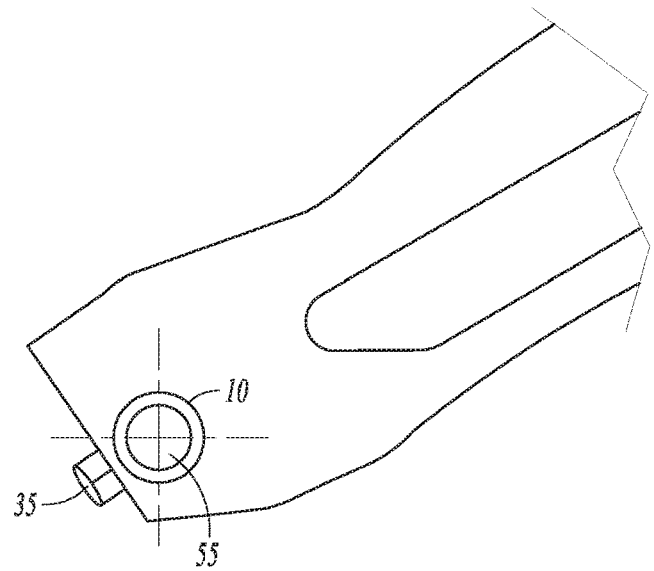
Figure 10C:
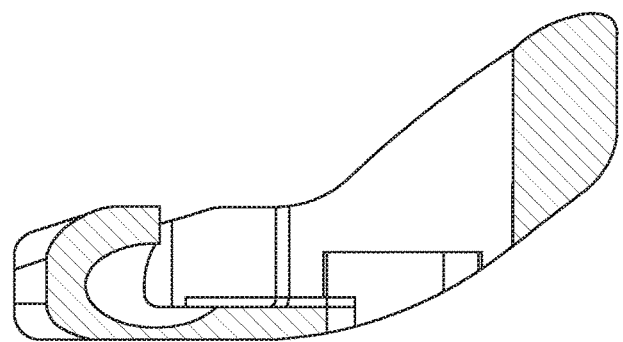
Figure 11:
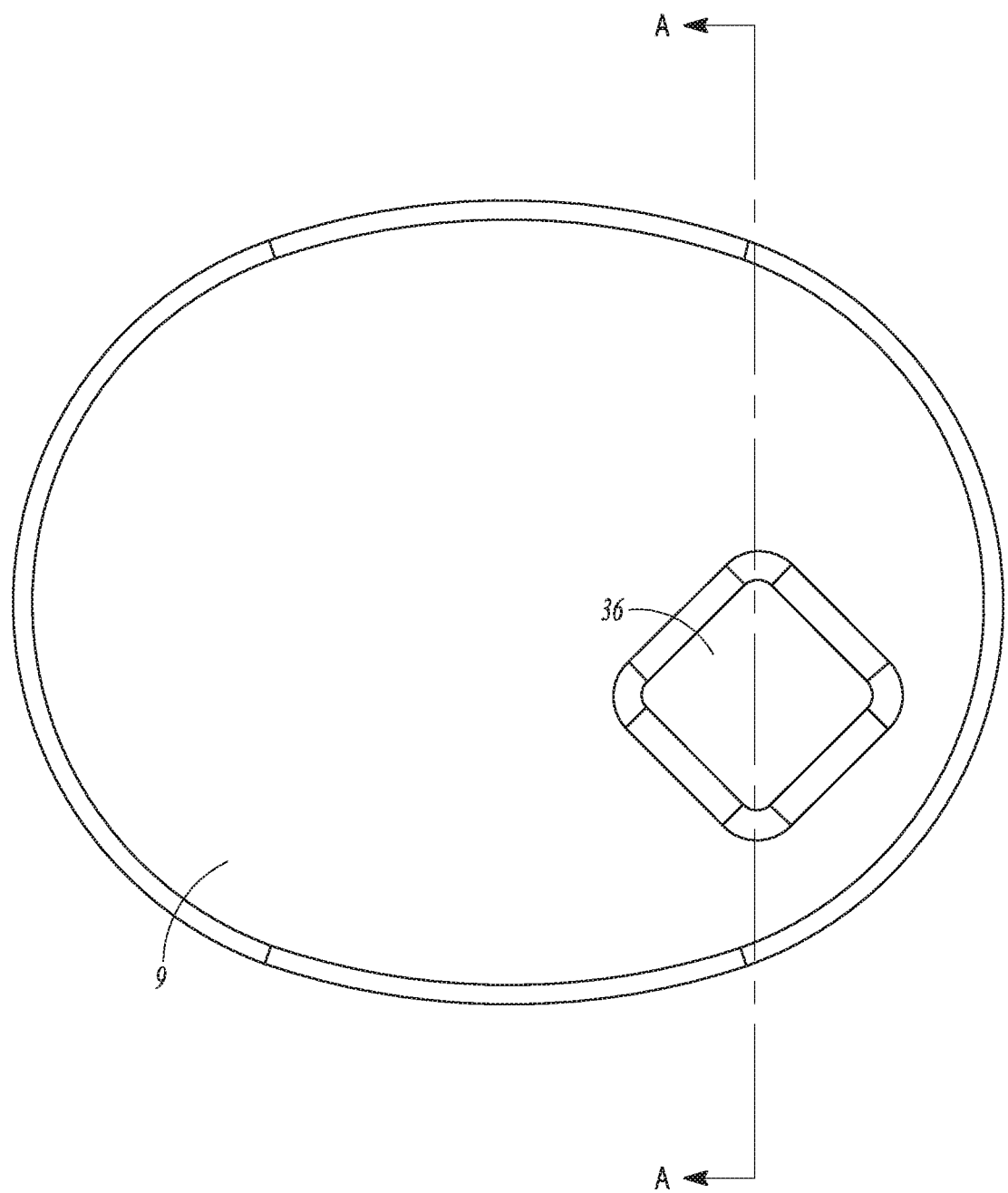
FIG. 11 illustrates a view of a right strike plate, as constructed in accordance with at least one embodiment.
Figure 12:
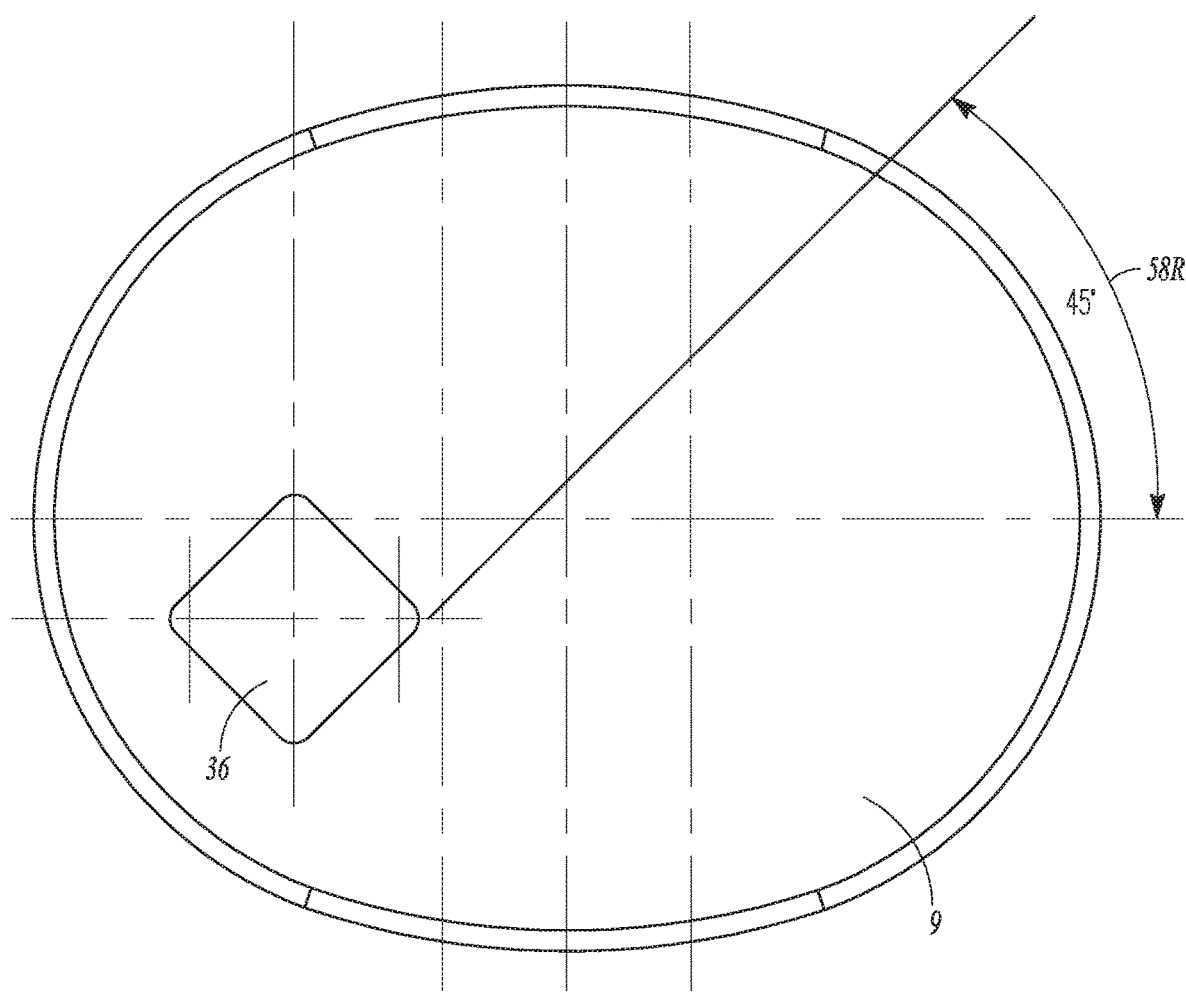
FIG. 12 illustrates a view of a right strike plate, as constructed in accordance with at least one embodiment.
Figure 14A:
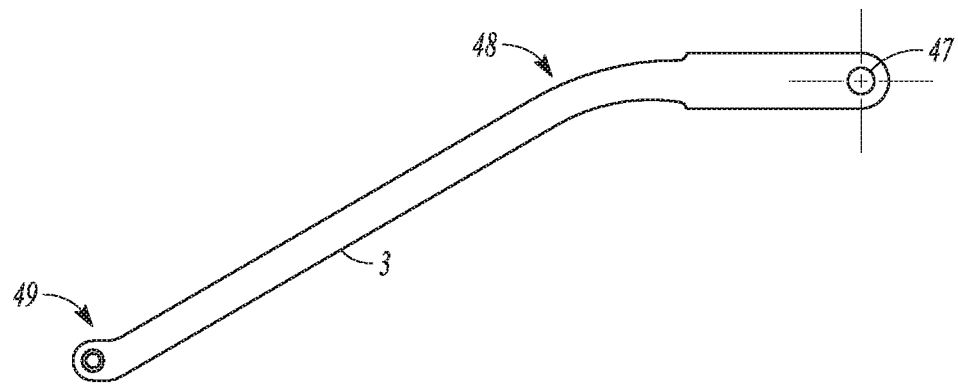
FIGS. 14A, B illustrate side views of a right transfer bar, as constructed in accordance with at least one embodiment.
Figure 14B:
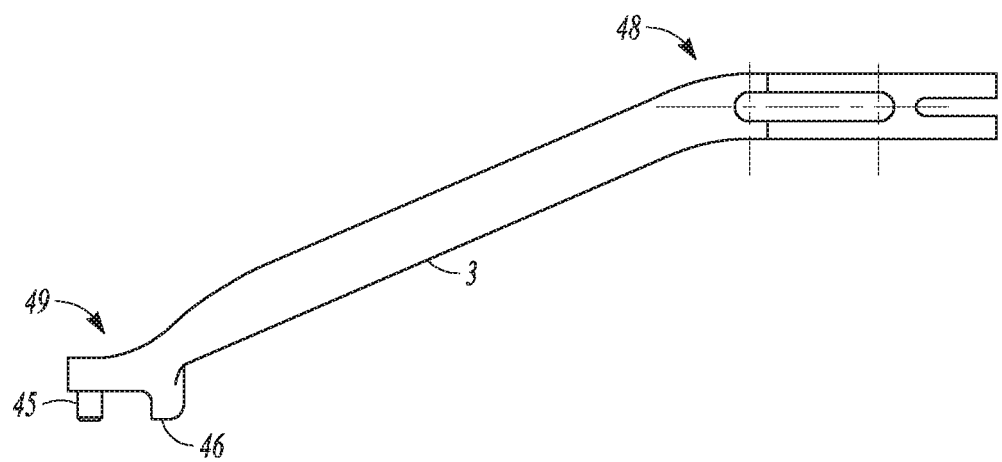
Figure 15:
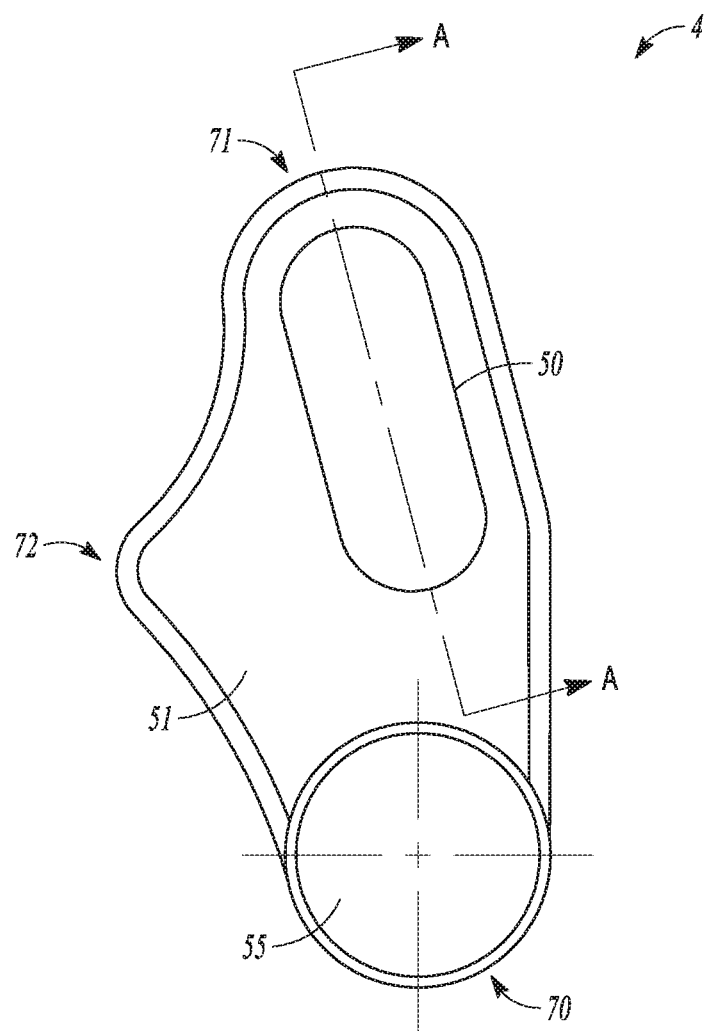
FIG. 15 illustrates a front view of right cam, as constructed in accordance with at least one embodiment.
Figure 16A:
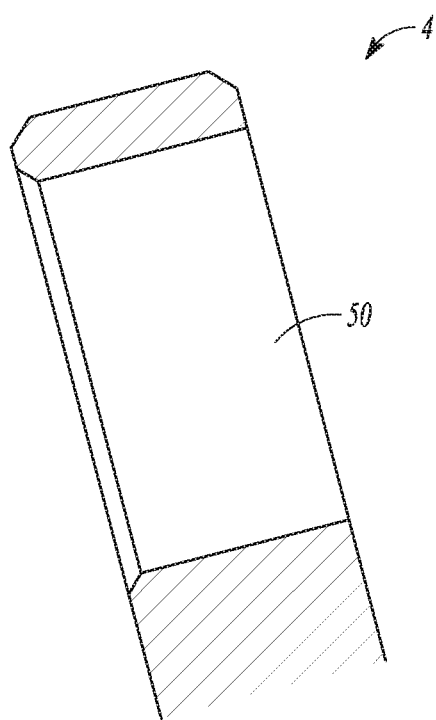
FIGS. 16A, B illustrate a cross-sectional view of section A-A of FIG. 15, and a side view of the cam of FIG. 15.
Figure 16B:
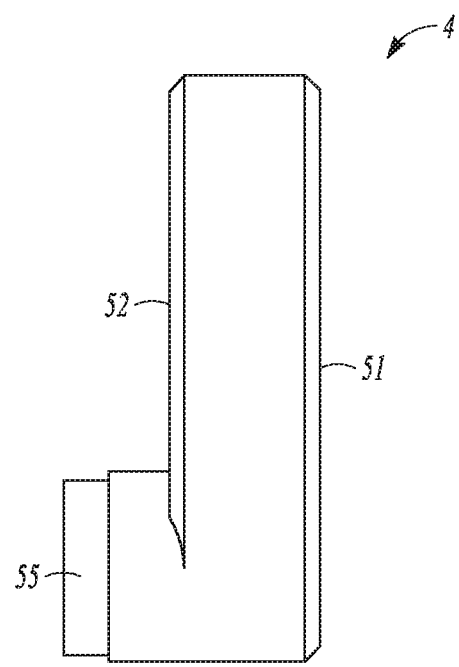
Figure 22:
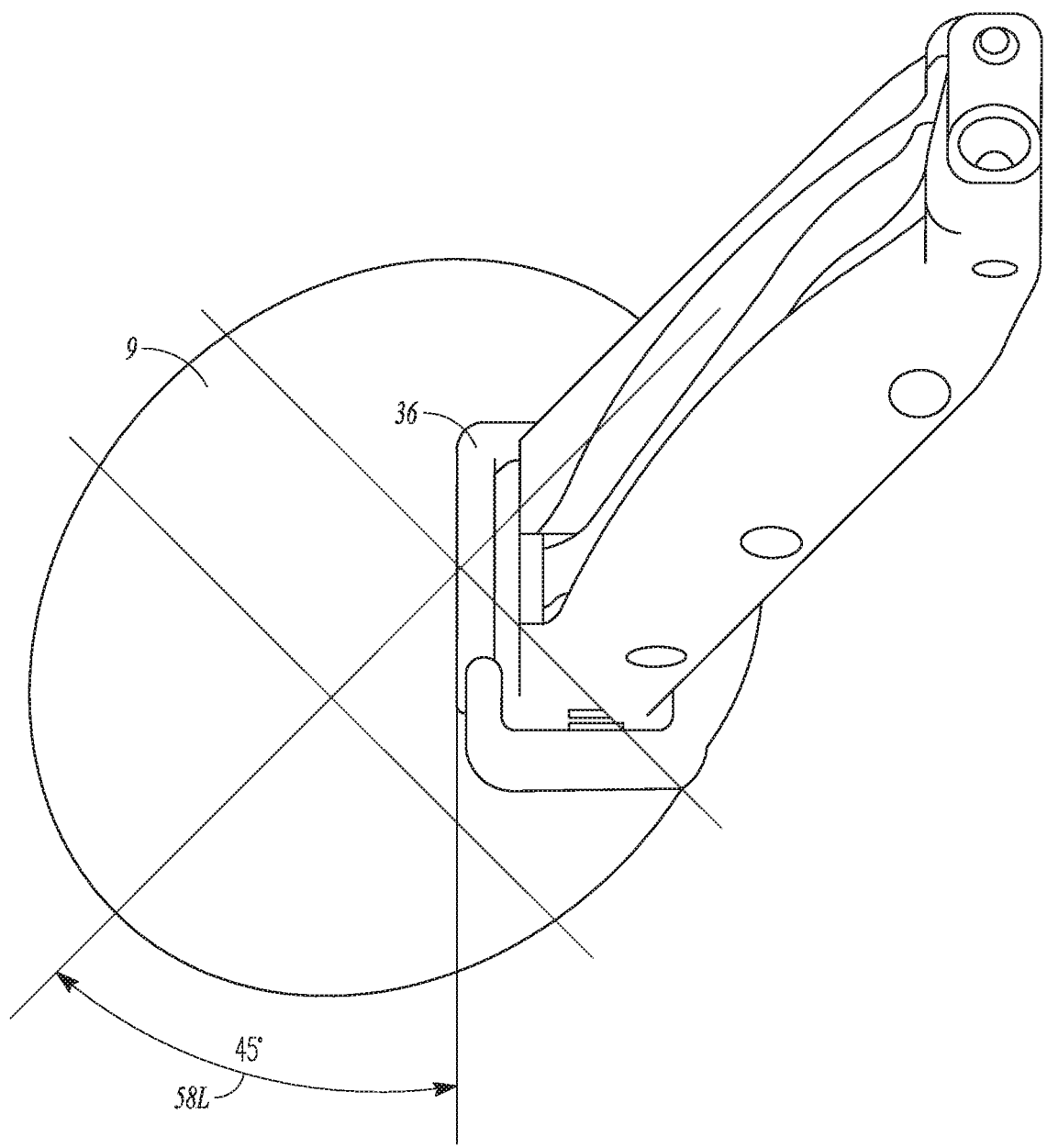
FIG. 22 illustrates an isometric view of a left tool handle, as constructed in accordance with at least one embodiment.
Figure 23A:
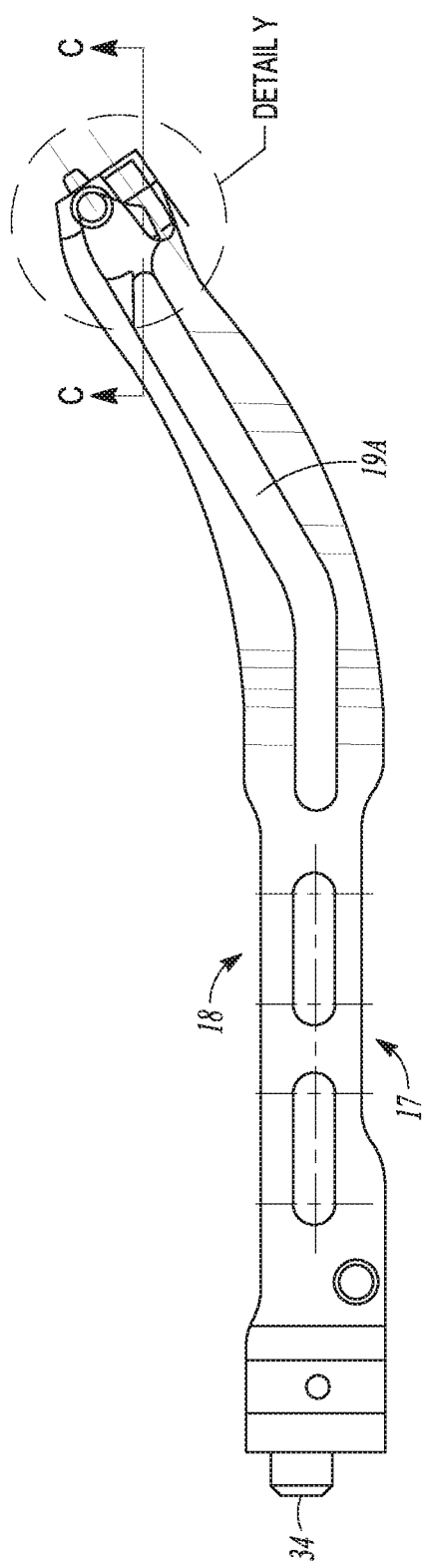
FIGS. 23A, B illustrate side views of a frame of the left tool handle, as constructed in accordance with at least one embodiment.
Figure 23B:
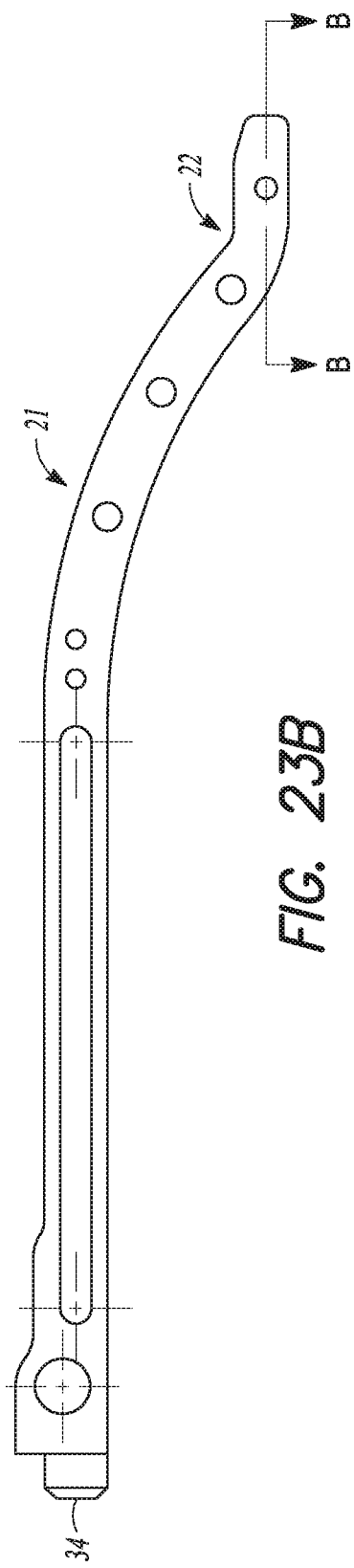
Figure 24:
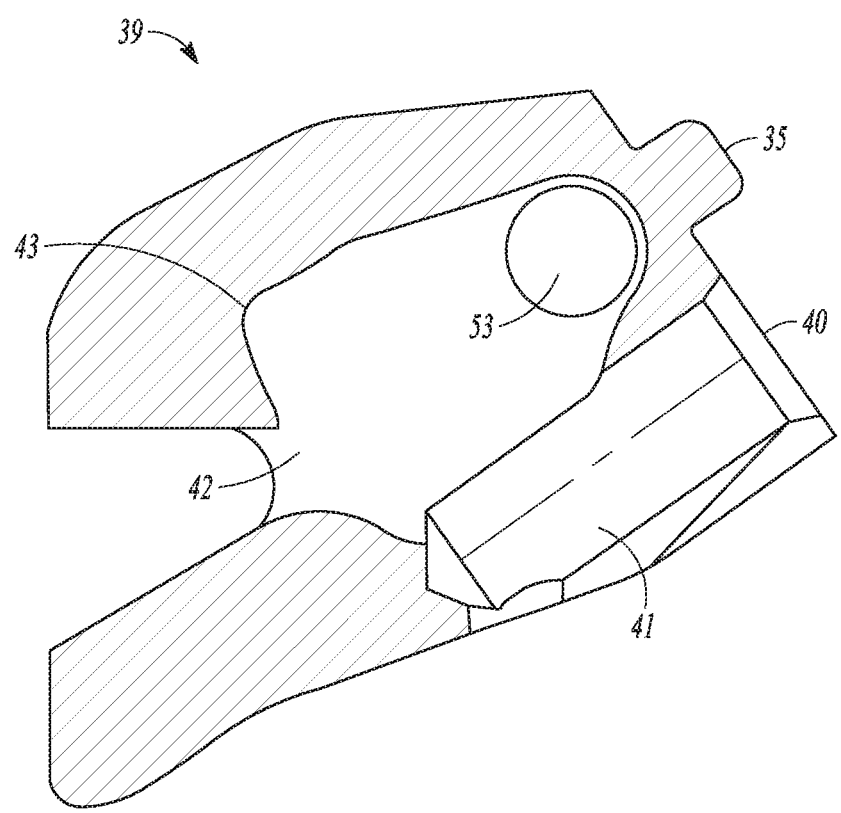
FIG. 24 illustrates a detailed view of section B-B of FIG. 23B.
Figure 25:
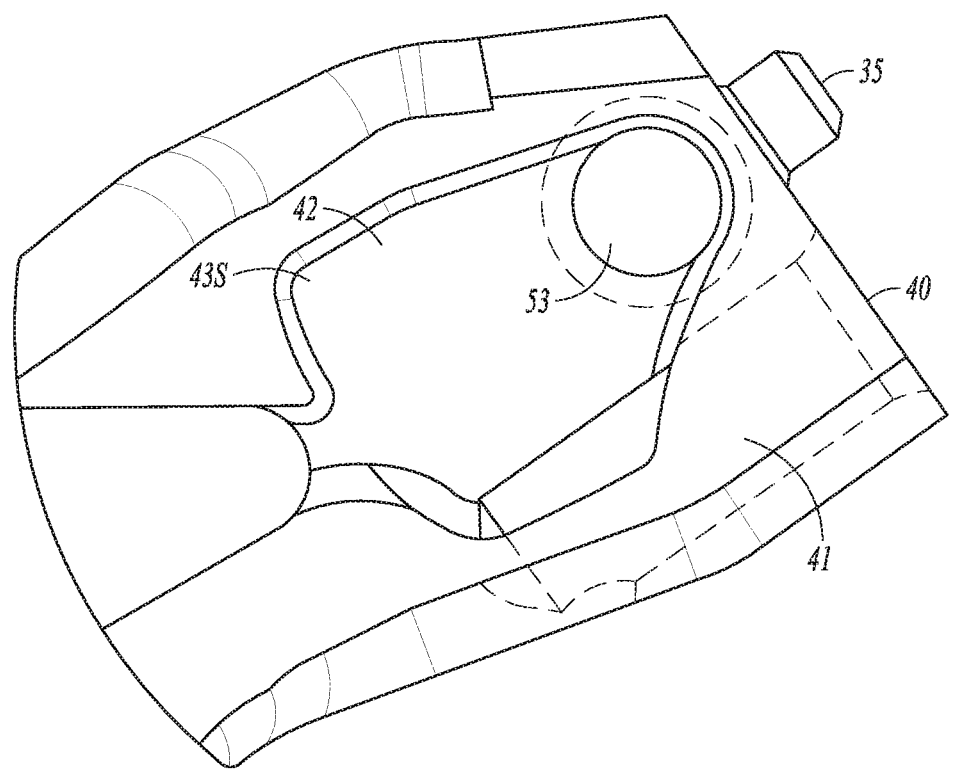
FIG. 25 illustrates a detailed view of section Y of FIG. 23A.
Figure 26A:
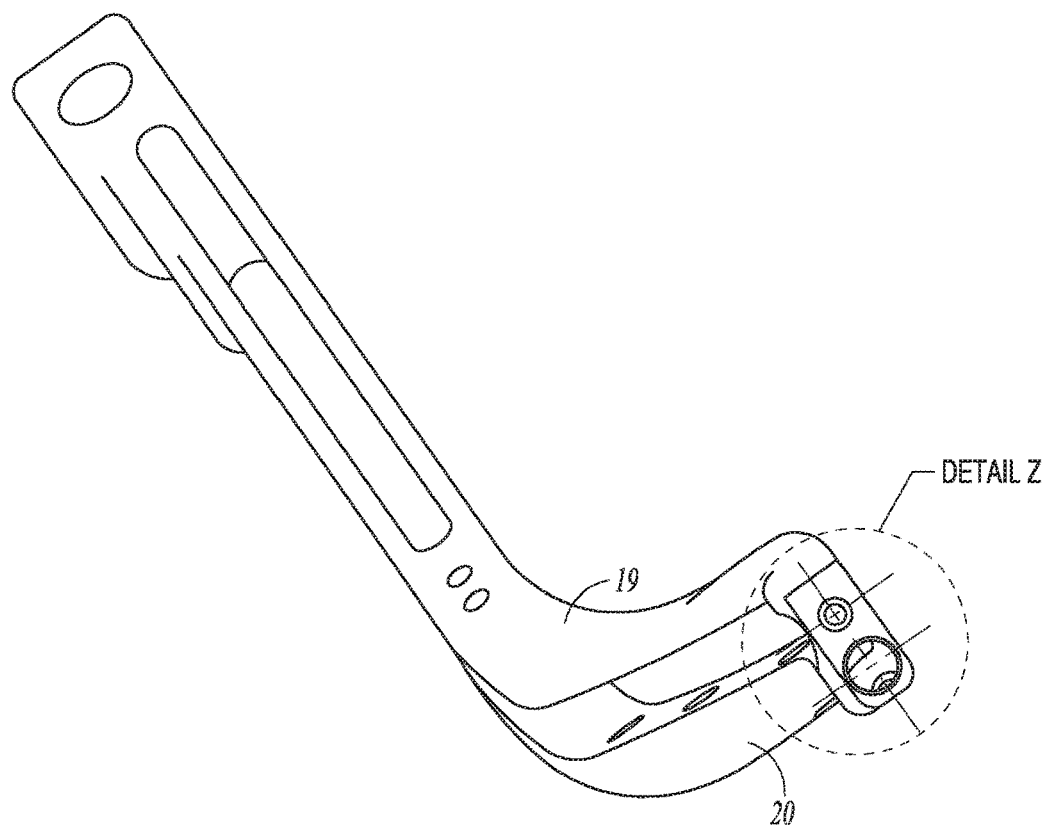
FIGS. 26A, B illustrate isometric views of a frame of a left tool handle, as constructed in accordance with at least one embodiment.
Figure 26B:
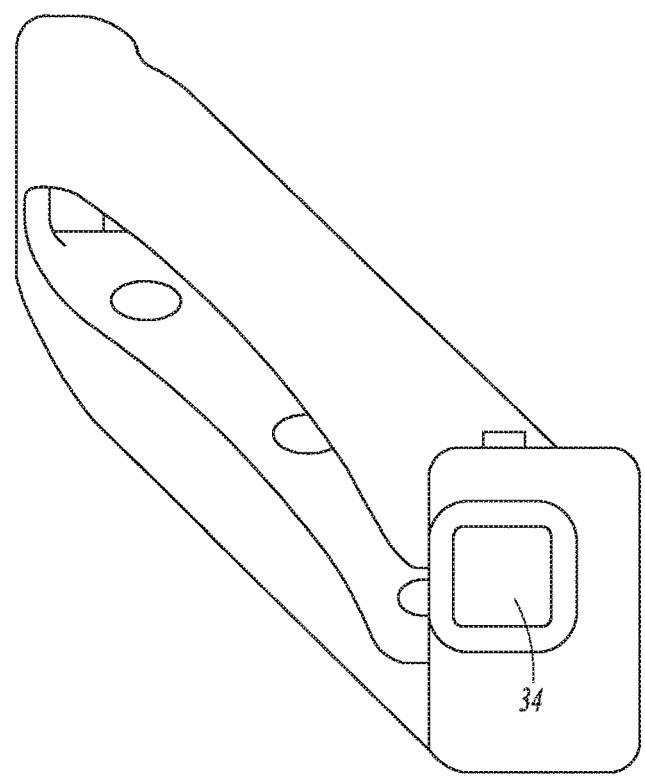
Figure 27A:
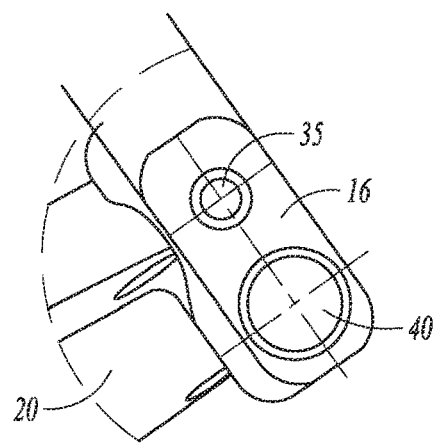
FIGS. 27A, B, C illustrate detailed views of section Z of FIG. 26A, and section C-C of FIG. 23A.
Figure 27B:
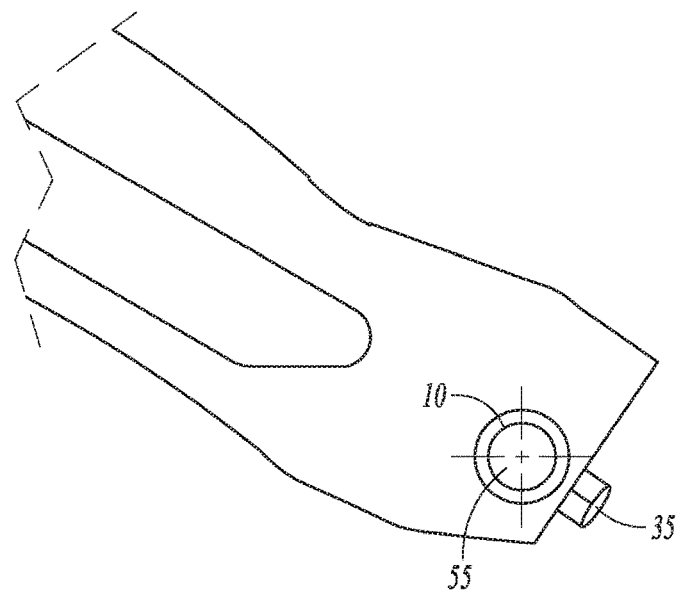
Figure 27C:
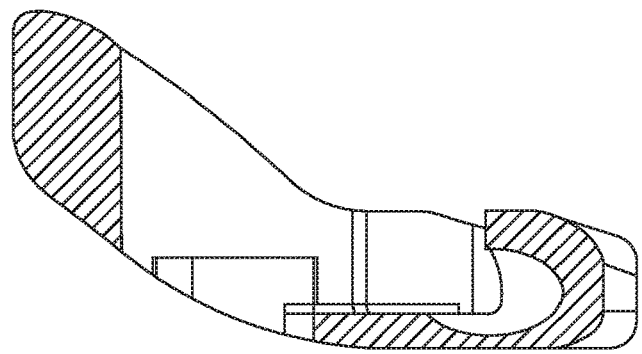
Figure 28:
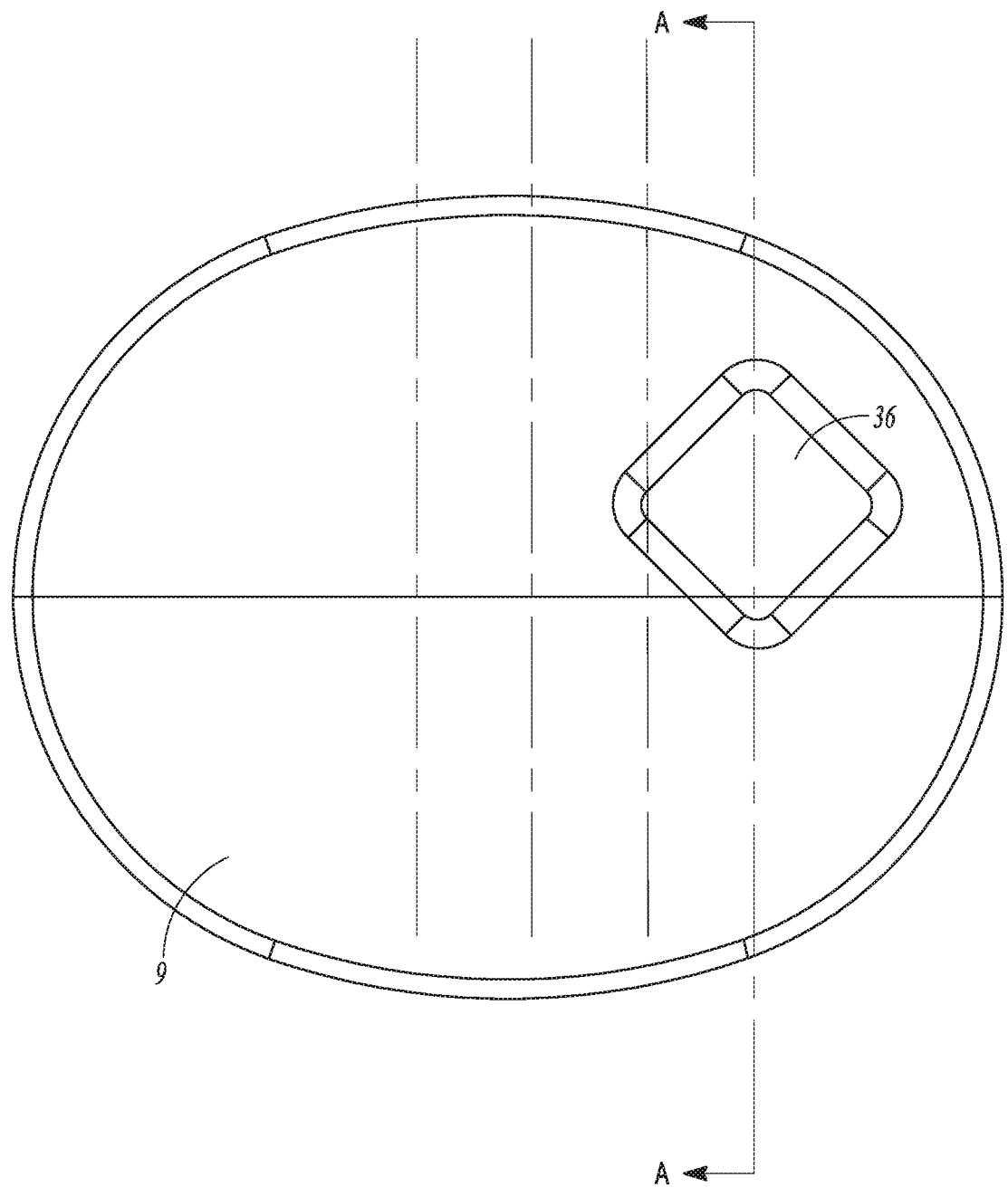
FIG. 28 illustrates a view of a left strike plate, as constructed in accordance with at least one embodiment.
Figure 29:
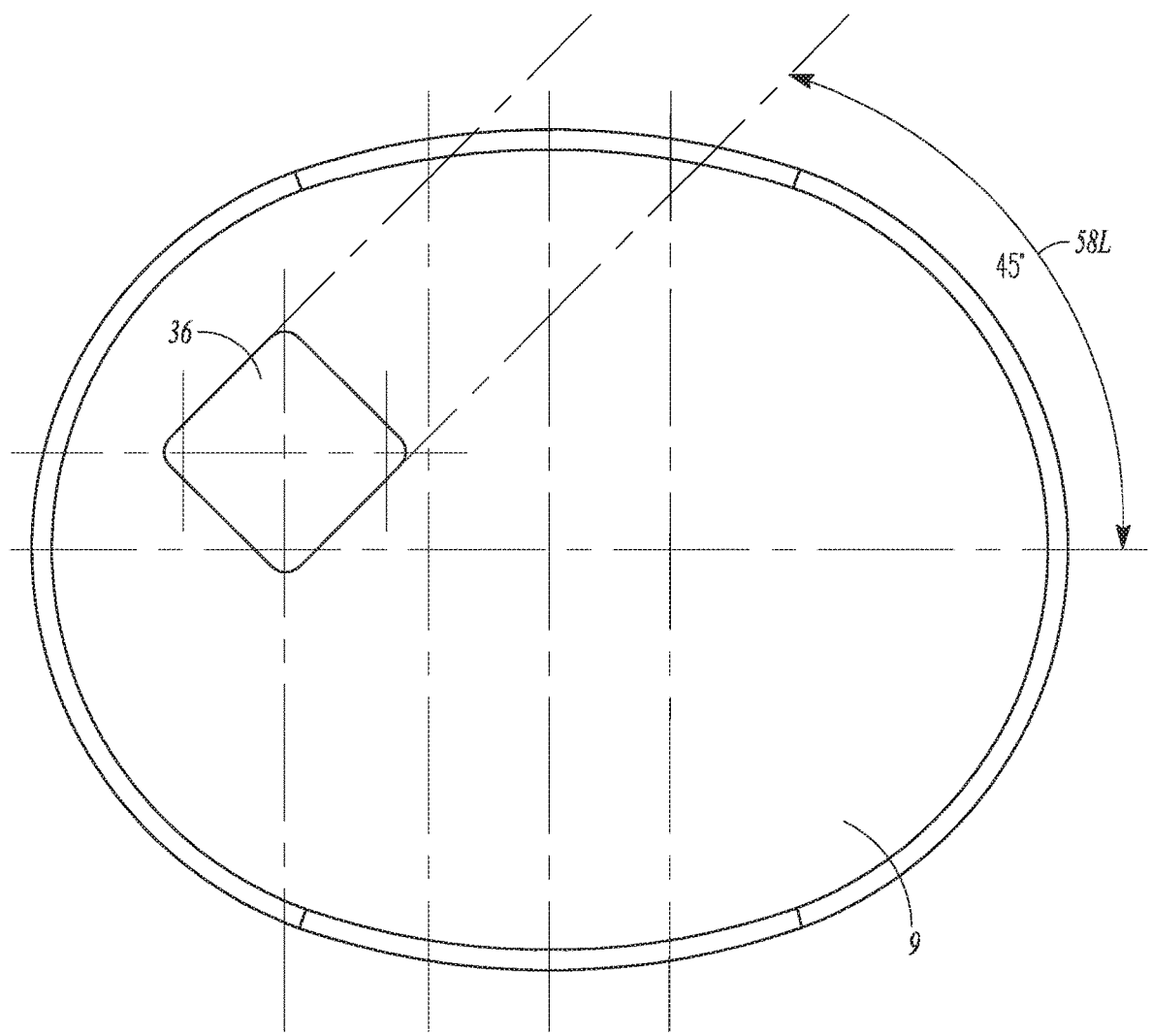
FIG. 29 illustrates a view of a left strike plate, as constructed in accordance with at least one embodiment.
Figure 31A:
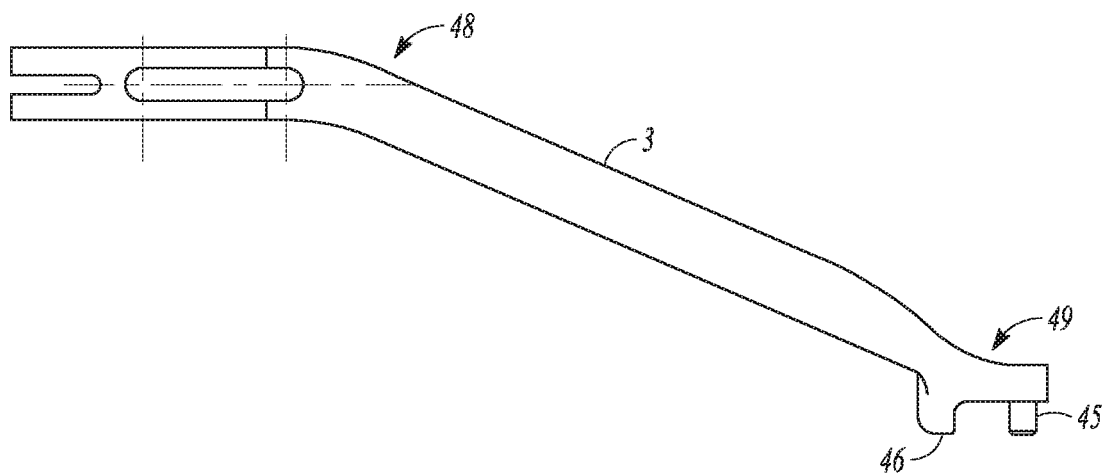
FIG. 31A, B illustrate side views of a left transfer bar, as constructed in accordance with at least one embodiment.
Figure 31B:
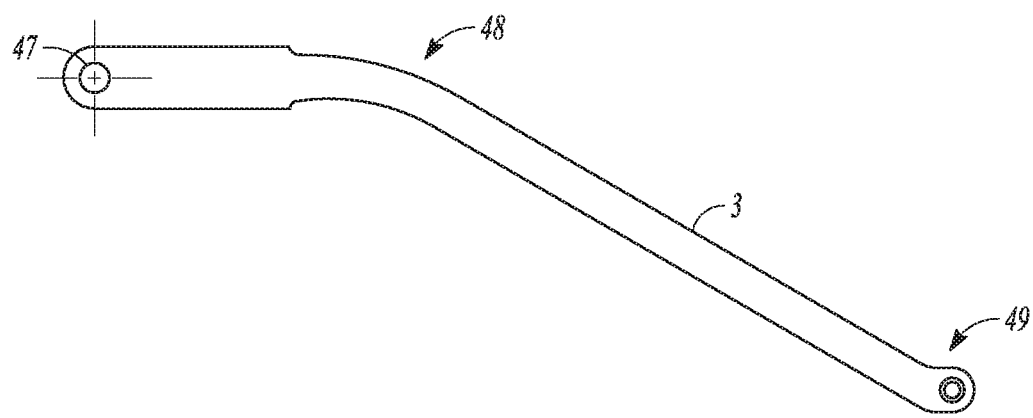
Figure 32:
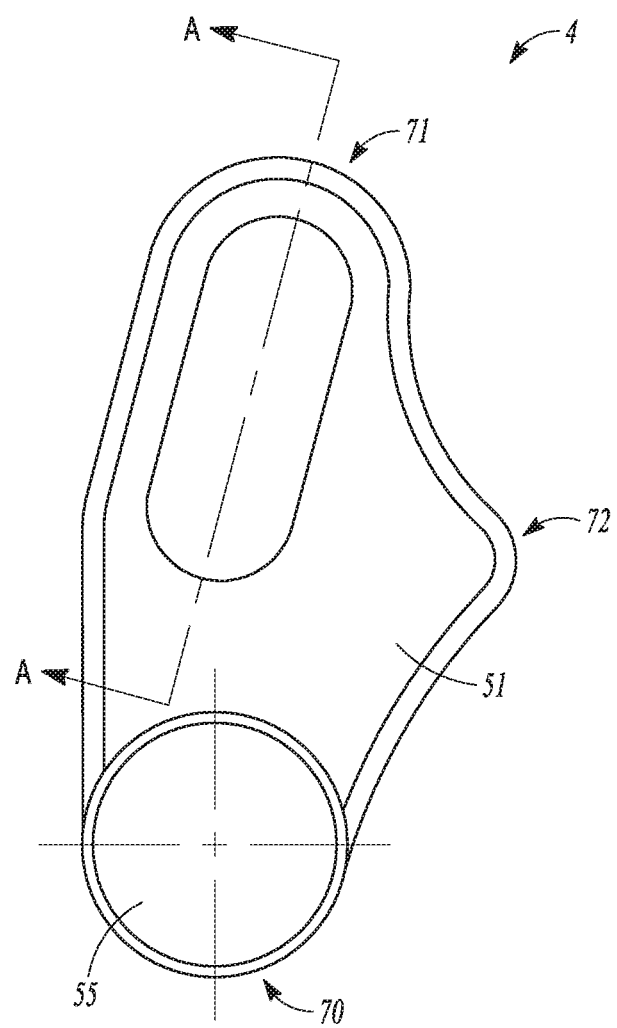
FIG. 32 illustrates a front view of a left cam, as constructed in accordance with at least one embodiment.
Figure 33A:
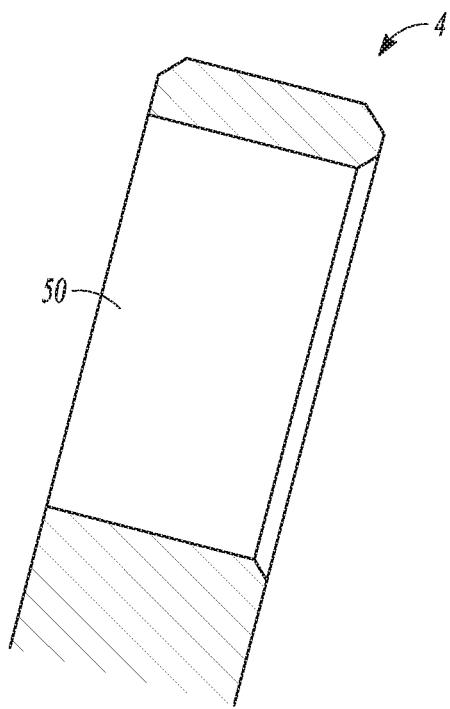
FIGS. 33A, B illustrate a cross-sectional view of section A-A of FIG. 32, and a side view of the cam of FIG. 32.
Figure 33B:
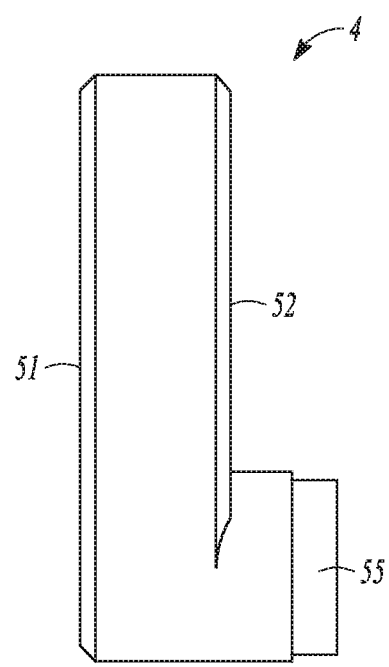
Figure 34A:
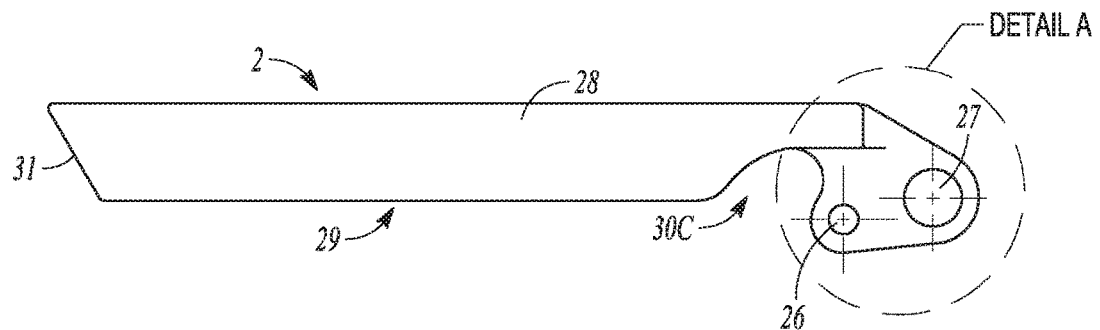
FIGS. 34A, B, C illustrate respective side, top, and side views of a lever, as constructed in accordance with at least one embodiment.
Figure 34B:
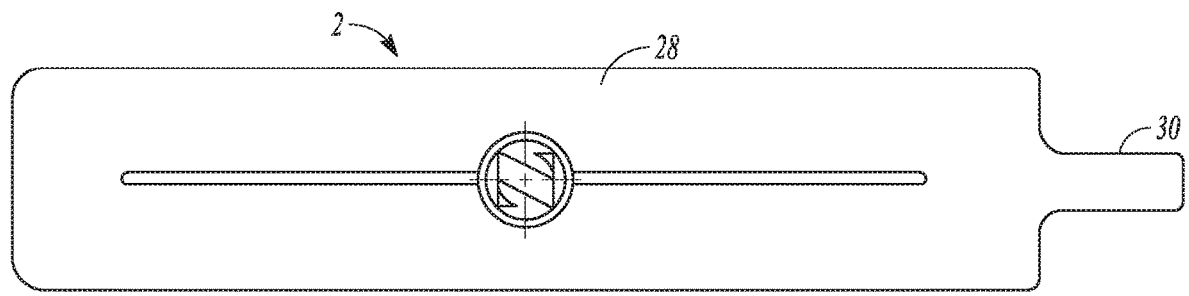
Figure 34C:
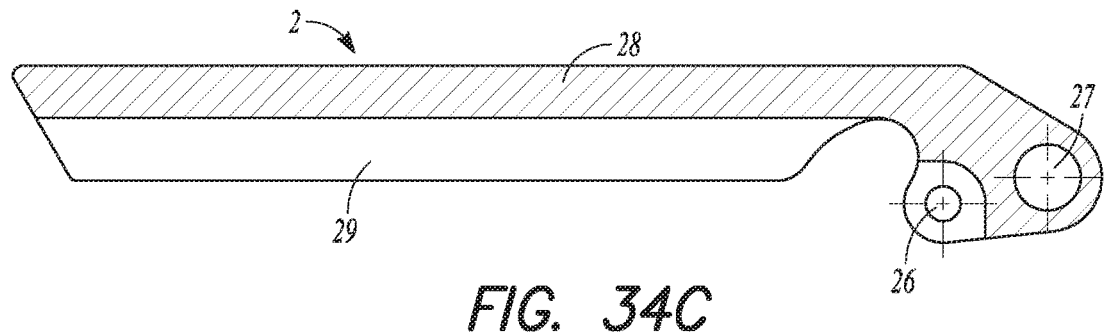
Figure 35A:
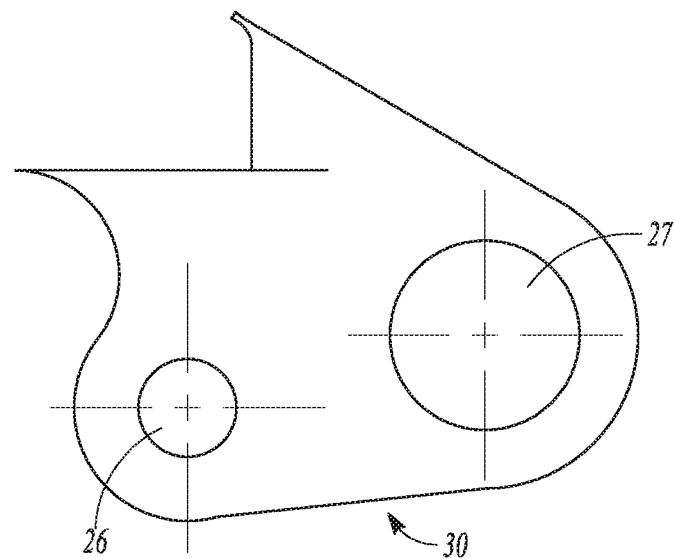
FIGS. 35A, B illustrate detailed views of section A of FIG. 34A, and a lever pivot end view of the lever illustrated in FIG. 34C, section B-B.
Figure 35B:
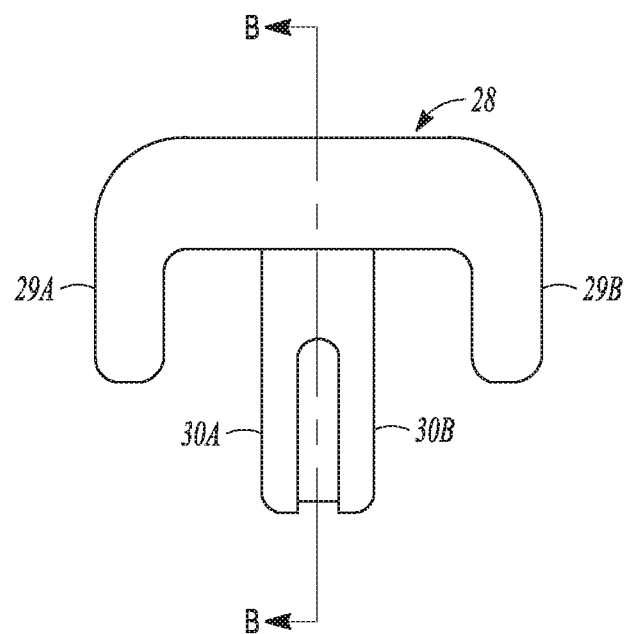
Figure 36A:
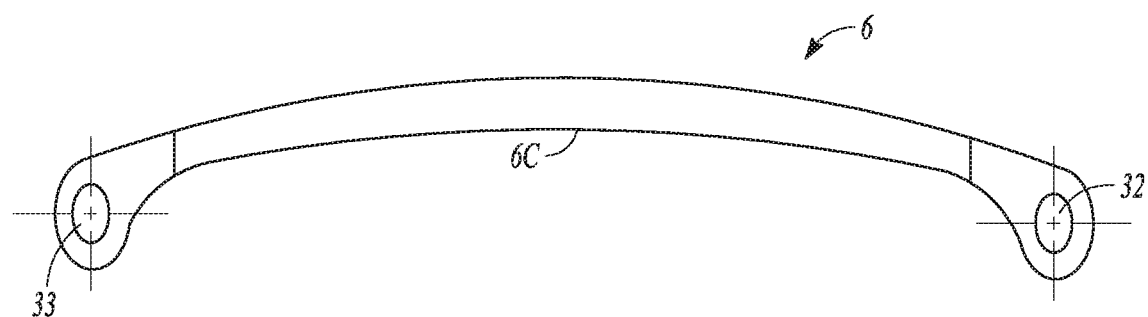
FIGS. 36A, B illustrate respective side and top views of a spring, as constructed in accordance with at least one embodiment.
Figure 36B:
Figure 37A:
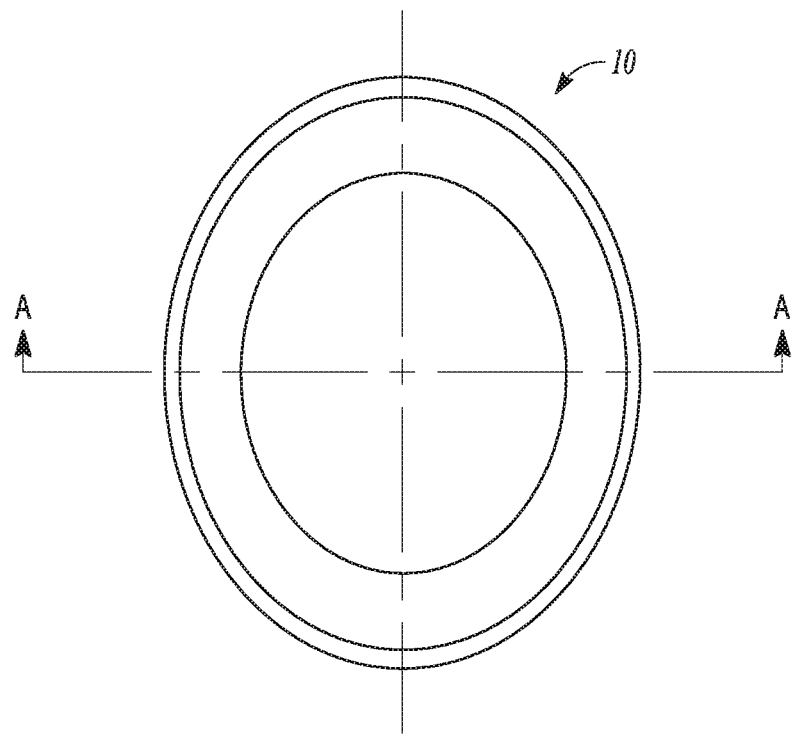
FIGS. 37A, B illustrate respective top view, and cross-sectional view through section A-A, of a washer, as constructed in accordance with at least one embodiment.
Figure 37B:
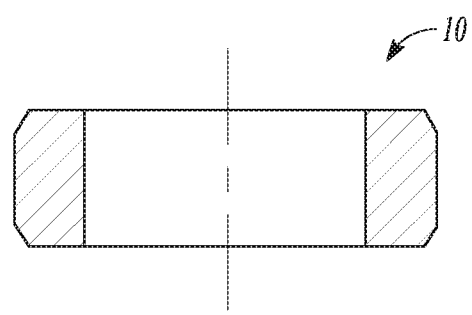
Figure 38A:
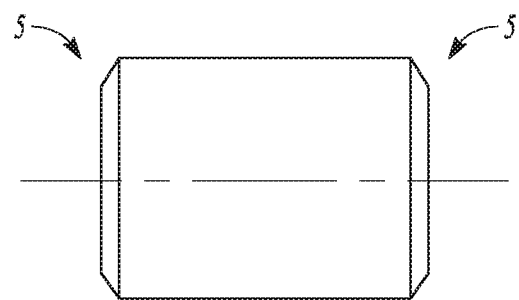
FIGS. 38A, B illustrate side views of a short pin, as constructed in accordance with at least one embodiment.
Figure 38B:
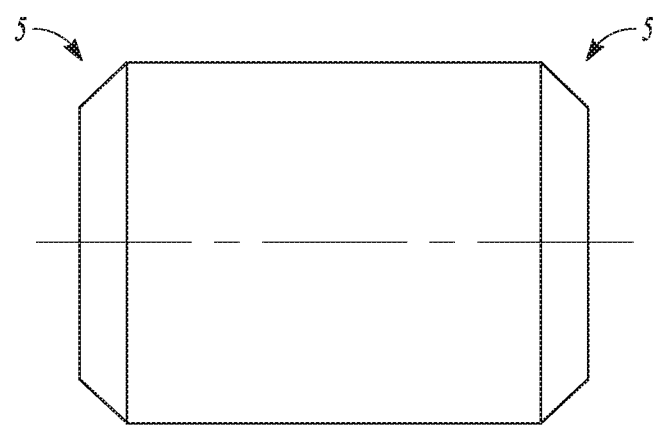
Figure 39A:
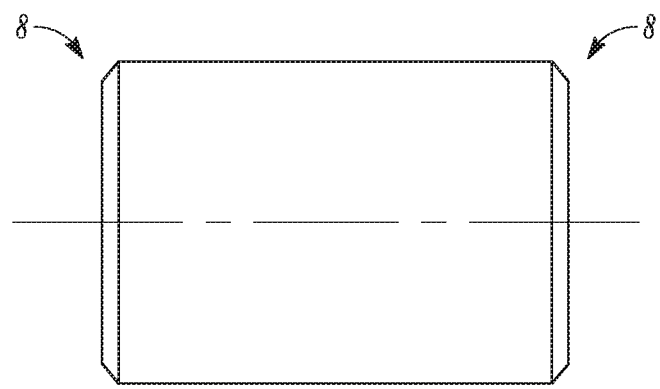
FIGS. 39A, B illustrate respective side views of a pivot pin and a long pin, as constructed in accordance with at least one embodiment.
Figure 39B:
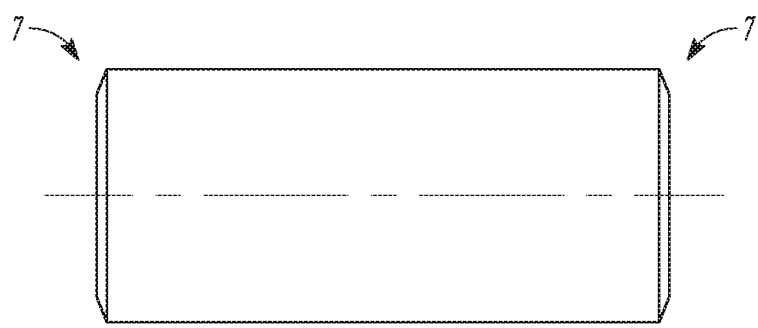
Figure 40:
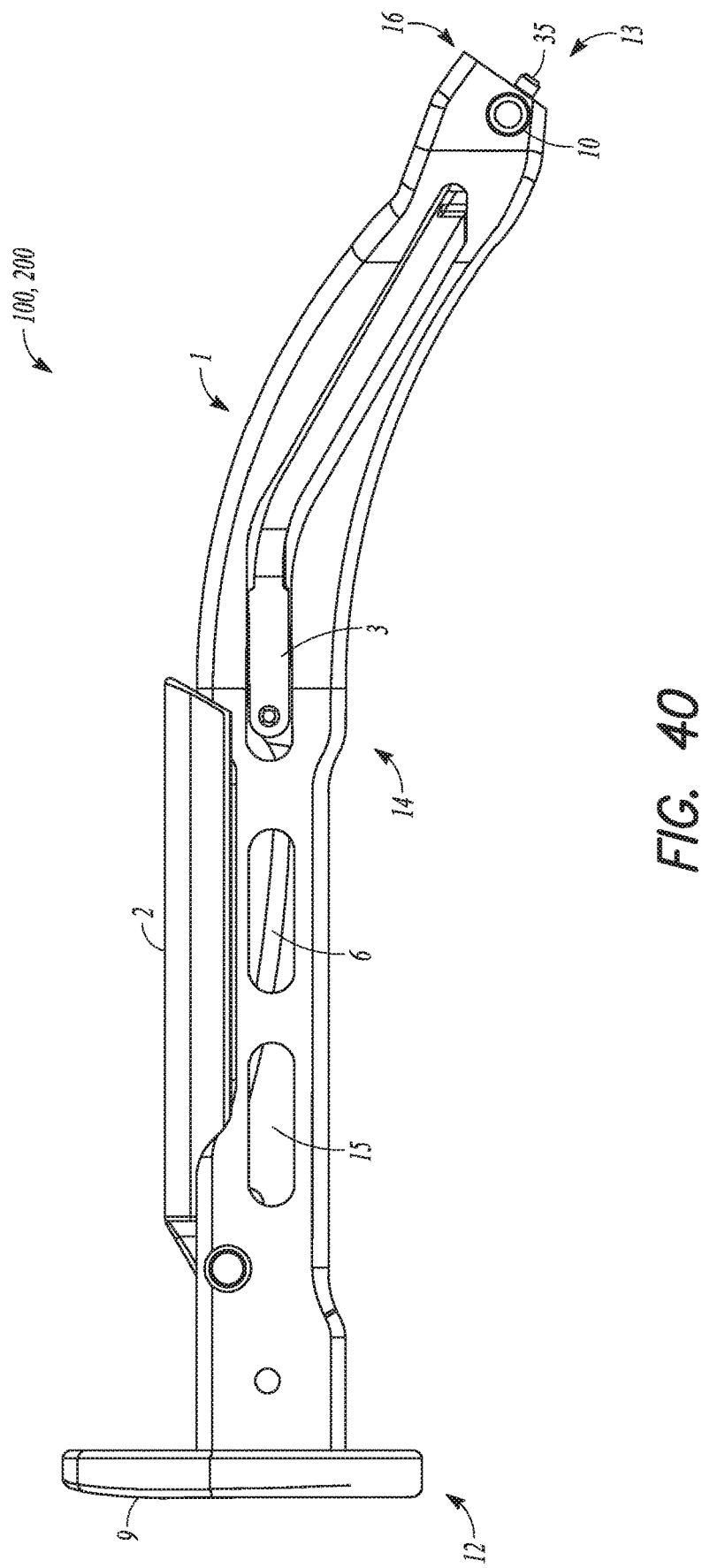
FIG. 40 illustrates a perspective view of a left handle assembly.

FIGS. 5 and 22 illustrate, respectively, the right tool handle assembly 100 and the left tool handle assembly 200, with the optional strike plate 9 disposed at the proximal end 12, which can be configured in any size and shape to receive an impacting tool (not shown). As illustrated in the embodiments, the strike plate 9 can be an ellipsis, or a generally ovoid or circular shape. The strike plate 9 (also illustrated in FIGS. 11, 12, 13A, and 13B, and FIGS. 28, 29, 30A, and 30B), can have a depth 9D (best illustrated in FIGS. 13A, 13B, 30A, and 30B), and a front surface 37 and a back surface 38, the front surface having a strike plate aperture 36 configured to receive an engagement portion of body 1, such as a proximal end post 34 (best seen in FIGS. 4B and 21B). The depth 9d may not be uniform across the front surface 37, for example the strike plate front surface 37 can be domed (as seen in FIGS. 1, 13A, 18, and 30A). The strike plate aperture can be oriented at an angle 58 with respect to the longitudinal axis 57 of the proximal end 12 of the body 1. As best illustrated in FIGS. 12 and 29, respectively, the right strike plate can be oriented at a right strike plate angle (58R) and the left strike plate can be oriented at left strike plate angle (58L). The strike plate angle 58 can be any angle desired for translation of the striking or impacting force directed to the strike plate 9 to impact a tool head 59 engaged at the distal end 13 of the body 1. In various examples, strike plate angles 58 can include angles within the range 35 degrees to 45 degrees, inclusive.

FIGS. 2-3 and 19-20 illustrate an embodiment of a tool handle assembly 100, 200 in a double-offset configuration. Each of the engaging arm 20 and the receiving arm 19 can comprise a first curved portion 21 disposed in the intermediate translation region 14, and a second curved portion 22 adjacent the nose 16. A curve 22a of the second curved portion can be configured such that the tool head 59 will be engaged with the body 1 in a plane having a longitudinal axis 61 parallel to the longitudinal axis 57 of the proximal end 12.

As can be seen in FIGS. 6A, 6B, 14A, 14B, 23A, 23B, 31A, and 31B, a translation bar 3 can comprise a first curved portion 48 and a second curved portion 39 that generally correspond to the first curved portion 21 and the second curved portion 22 of the body 1. A linking mechanism can include the translation bar 3 and it should be noted that the second curved portion 49 of the translation arm 3 can include one or more means (such as, for example, posts 45, 46) configured to engage the locking mechanism portion 39, thereby facilitating the locking engagement of the mating member 60 in the receiving chamber 41.

In an embodiment, the tool handle assemble and related method of using any one (or portion of any one) or any combination of embodiments of a tool handle assembly described herein, can optionally be configured such that all elements or options recited are available to use or select from.

The above Detailed Description includes references to the accompanying drawings, which form a part of the Detailed Description. The drawings show, by way of illustration, specific embodiments in which the handle assembly and related methods can be practiced. These embodiments are also referred to herein as "examples." While certain examples are shown and described with respect to a left or a right handle orientation, it is to be appreciated that the present disclosure is equally applicable to both the left and right handles.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, "anterior" refers to a direction generally toward the front of a patient, "posterior" refers to a direction generally toward the back of the patient, "medial" refers to a direction generally toward the middle of the patient, and "lateral" refers to a direction generally toward the side of the patient. In this document, the phrase "anterior/posterior direction" is used to include an anterior to posterior direction or a posterior to anterior direction.

In the appended claims, the terms "including" and "in which" are used as the plain-English equivalents of the respective terms "comprising" and "wherein." The terms "including" and "comprising" are open-ended, that is, an apparatus, system, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. In the event of inconsistent usages between this document and any document so incorporated by reference, the usage in this document controls.

The Abstract is provided to allow the reader to quickly ascertain the nature of the technical disclosure. It is submitted with the understanding that it will not be used to interpret or limit the scope or meaning of the claims.

REFERENCE LEGEND

1 Body
2 Lever
3 Translation Bar
4 Cam
5 Pivot Pin
6 Elastic Member/Spring
7 Long Pin(s)
8 Translation Pivot Pin
9 Strike Plate
10 Washer
11 Lever Hinge Pin
12 Body Proximal End
13 Body Distal End
14 Body Intermediate Translation Region
15,19A Chamber
16 Nose
17 Top 18 Bottom
19 Receiving Arm
20 Engaging Arm
21 First Arcuate Portion
22 Second Arcuate Portion
23 Horizontal Offset Angle
24 Vertical Offset Angle
25 Long Pin Receiving Holes
26 Lever First Hole (Lever/Spring)
27 Lever Second Hole (Lever/Frame Hinge)
28 Lever Top Portion
29 Lever Side Portion
30 Lever Pivot End
31 Lever Angled End
32 Spring First Pin Hole (Spring/Lever)
33 Spring Second Pin Hole (Spring/Translation Bar)
34 Strike Plate Post
35 Tool Mating Post
36 Strike Plate Aperture
37 Strike Plate Front Surface
38 Strike Plate Back Surface
39 Locking Mechanism Portion
40 Tool Head Receiving Aperture
41 Receiving Chamber
42 Ramp Feature
43 Ramp Track
43s Ramp Track Surface
44 Lever Pivot Point
45 Translation Bar Cam Track Post
46 Translation Bar Ramp Post
47 Translation Pivot Hole
48 Translation Arm First Curved Portion
49 Translation Arm Second Curved Portion
50 Cam Track Aperture
51 Cam Front Surface
52 Cam Back Surface
53 Cam Pivot Hole
54 Cam Locking Edge
55 Cam Shaft
56 Offset Angle
57 Proximal End Longitudinal Axis
58 Strike Plate Angle
59 Tool Head
60 Tool Feature/Mating Member
61 Tool Head Longitudinal Axis
100 Right Handle Assembly
200 Left Handle Assembly

What is claimed is:

1. A surgical tool handle assembly, comprising:
a housing having a receiving chamber configured to receive a portion of a surgical tool;
a ramp feature formed in a wall of the housing adjacent to the receiving chamber, the ramp feature comprising a ramp surface and a ramp track angled with respect to a longitudinal axis of the housing;
a cam comprising a peripheral surface configured to move a distance along the ramp surface to lockingly engage the cam with the surgical tool; and
a translation member configured to move the cam the distance along the ramp surface to lockingly engage the surgical tool, wherein the cam includes an aperture defining a generally oval or ovoid cam track, and the translation member includes a cam post configured to engage the cam track.

2. The surgical tool handle assembly of claim 1, further comprising a lever configured to move the cam the distance along the ramped surface.

3. The surgical tool handle assembly of claim 1, wherein the ramp surface is angled between 10 degrees and 70 degrees with respect to the longitudinal axis of the housing.

4. The surgical tool handle assembly of claim 1, wherein the ramp feature is formed within a side wall of the housing.

5. The surgical tool handle assembly of claim 1, wherein the ramp feature and the translation member define an angular relationship providing a mechanical advantage for locking engagement of the cam with the surgical tool.

6. The surgical tool handle assembly of claim 1, wherein the translation member includes a ramp post configured to transfer a force to the ramp track.

7. The surgical tool handle assembly of claim 1, wherein the ramp track is angled between 10 degrees and 70 degrees with respect to the longitudinal axis of the housing.

8. The surgical tool handle assembly of claim 1, wherein the cam post is movable within the cam track.

9. A method for securing a surgical tool to a handle, comprising:
providing or obtaining a handle assembly including:
a handle body having a top and a bottom;
a ramp formed in a wall of the body and extending in a direction between the top and the bottom of the body, the ramp angled with respect to a longitudinal axis of the body;
a receiving chamber adjacent to the ramp and configured to receive a handle mating portion of the surgical tool;
a cam; and
a translation member having a first post engaged with the ramp and a second post engaged with the cam;
receiving the handle mating portion of the surgical tool into the receiving chamber when the translation member is in a first position; and
moving the cam along a surface of the ramp and into locking engagement with the handle mating portion of the surgical tool.

10. The method of claim 9, wherein the step of moving further comprises actuating the translation member into a second position to move the cam into locking engagement with the handle mating portion of the surgical tool.

11. The method of claim 9, wherein the first post defines an angular relationship with the ramp, the method further comprising providing a mechanical advantage for locking engagement of the cam with the handle mating portion of the surgical tool through the angular relationship between the first post and the ramp.

12. A surgical tool handle assembly, comprising:
a housing defining a chamber configured to receive a portion of a surgical tool;
a cam disposed to lockingly engage the surgical tool when the surgical tool is received within the chamber;
a ramp formed in a side wall of the housing adjacent to the chamber, the ramp extending in a direction between a top and a bottom of the housing and comprising a ramp track and a ramp surface angled with respect to a longitudinal axis of the housing; and
a translation member comprising a first post engaged with the cam and a second post engaged with the ramp track, the cam disposed to travel a distance on the ramp surface during locking engagement of the cam with the surgical tool.

13. The tool handle assembly of claim 12, wherein the ramp surface and the ramp track are disposed at an angle between 10° and 70° relative to the longitudinal axis of the housing.

14. The tool handle assembly of claim 12, wherein the translation member comprises a second post configured to transfer a force to the ramp track.

15. The tool handle assembly of claim 12, wherein the first post is configured to move within a track formed in the cam during locking engagement of the cam with the surgical tool.

16. The tool handle assembly of claim 12, wherein the cam comprises a generally oval or ovoid shape extending between a first end and a second end of the cam, and a locking feature of the cam is disposed between the first end and the second end.

17. The tool handle assembly of claim 12, wherein the cam comprises an oval or ovoid cam track, the first post configured to move within the cam track.

* * * * *